United States Patent
Basile

(10) Patent No.: US 9,063,150 B2
(45) Date of Patent: Jun. 23, 2015

(54) METHOD FOR DETECTION OF ANTIGEN-SPECIFIC ANTIBODIES IN BIOLOGICAL SAMPLES

(75) Inventor: Alison Jane Basile, Fort Collins, CO (US)

(73) Assignee: The United States of America as represented by the Secretary of the Department of Health and Human Services, Centers for Disease Control Prevention, Washington, DC (US)

(*) Notice: Subject to any disclaimer, the term of this patent is extended or adjusted under 35 U.S.C. 154(b) by 451 days.

(21) Appl. No.: 13/060,399

(22) PCT Filed: Aug. 25, 2009

(86) PCT No.: PCT/US2009/054916
§ 371 (c)(1),
(2), (4) Date: Feb. 23, 2011

(87) PCT Pub. No.: WO2010/036470
PCT Pub. Date: Apr. 1, 2010

(65) Prior Publication Data
US 2011/0151582 A1 Jun. 23, 2011

Related U.S. Application Data

(60) Provisional application No. 61/173,426, filed on Apr. 28, 2009, provisional application No. 61/208,168, filed on Feb. 19, 2009, provisional application No. 61/093,605, filed on Sep. 2, 2008.

(51) Int. Cl.
*G01N 33/564* (2006.01)
*G01N 33/569* (2006.01)
(Continued)

(52) U.S. Cl.
CPC .......... *G01N 33/6854* (2013.01); *G01N 33/564* (2013.01); *G01N 33/569* (2013.01); *G01N 33/585* (2013.01)

(58) Field of Classification Search
USPC ............... 435/5, 6, 7.1, 7.92, 287.2; 436/513, 436/517, 518, 524, 529, 533, 171, 172, 436/811; 422/73, 82.08, 82.09
See application file for complete search history.

(56) References Cited

U.S. PATENT DOCUMENTS 5,652,134 A * 7/1997 Maclachlan et al. .......... 435/339
5,741,654 A 4/1998 Michel et al.
(Continued)

OTHER PUBLICATIONS

Vignali. Multiplexed particle-based flow cytometric assays, Journal of Immunological Methods 243: 243-255 (2000).*
(Continued)

*Primary Examiner* — Gail R Gabel
(74) *Attorney, Agent, or Firm* — Klarquist Sparkman, LLP

(57) ABSTRACT

Disclosed herein is a rapid and universal assay for the detection of antigen-specific antibodies in biological samples. The assay allows for the detection of antigen-specific antibodies in any species, including species for which secondary antibodies or antisera have not been developed or are not available. Biological samples to be tested are directly labeled, such as with biotin, and contacted with antigen-bound microparticles. The presence of antigen-specific antibodies in the biological samples is detected using a binding partner for the label, such as a biotin binding partner, conjugated to a detectable label, such as a fluorophore. This improved test provides a total antibody assay that is capable of detecting all classes of antibodies simultaneously.

25 Claims, 12 Drawing Sheets

(51) Int. Cl.
*G01N 33/68* (2006.01)
*G01N 33/58* (2006.01)

(56) References Cited

U.S. PATENT DOCUMENTS

| | | | |
|---|---|---|---|
| 7,067,258 | B2 | 6/2006 | Esser et al. |
| 7,351,547 | B2 * | 4/2008 | Wong et al. ............... 435/7.92 |
| 2003/0134345 | A1 | 7/2003 | Brunner |
| 2003/0139322 | A1 | 7/2003 | Lam et al. |
| 2009/0068639 | A1 * | 3/2009 | Aizawa et al. ............... 435/5 |

OTHER PUBLICATIONS

Wong et al. Detection of Human Anti-Flavivirus Antibodies with a West Nile Virus Recombinant Antigen Microsphere Immunoassay, Journal of Clinical Microbiology 42 (1): 65-72 (Jan. 2004).*

Blitvich, et al., "Epitope-Blocking Enzyme-Linked Immunosorbent Assays for the Detection of Serum Antibodies to West Nile Virus in Multiple Avian Species," *J. Clin. Microbiol.*, vol. 41(3):1041-1047, 2003.

Bossart, et al., "Neutralization Assays for Differential Henipavirus Serology Using Bio-Plex Protein Array Systems," *J. Virol. Methods*, vol. 142:29-40, 2007.

Earley et al., "Report From a Workshop on Multianalyte Microsphere Assays," *Cytometry* vol. 50:239-242, 2002.

Johnson, et al., "Validation of a Microsphere-Based Immunoassay for Detection of Anti-West Nile Virus and Anti-St. Louis Encephalitis Virus Immunoglobulin M Antibodies," *Clin. Vaccine Immunol.*, vol. 14(9):1084-1093, 2007.

Johnson, et al., "Duplex Microsphere-Based Immunoassay for Detection of Anti-West Nile Virus and Anti-St. Louis Encephalitis Virus Immunoglobulin M Antibodies," *Clin. Diagn. Lab. Immunol.*, vol. 12(5):566-574, 2005.

Kellar et al., "Multiplexed Fluorescent Bead-Based Immunoassays for Quantitation of Human Cytokines in Serum and Culture Supernatants," *Cytometry* vol. 45:27-36, 2001.

Roberson et al., "Differentiation of West Nile and St. Louis Encephalitis Virus Infections by Use of Noninfectious Virus-Like Particles with Reduced Cross-Reactivity," *J. Clin. Microbiol.*, vol. 45(10):3167-3174, 2007.

Sellman et al., "Identification of Immunogenic and Serum Binding Proteins of *Staphylococcus epidermidis*," *Infect. Immun.*, vol. 73(10): 6591-6600, 2005.

Trainor et al., "Mutation Analysis of the Fusion Domain Region of St. Louis Encephalitis Virus Envelope Protein," *Virology*, vol. 360:398-406, 2007.

Vignali, D. A.A., "Mutiplexed Particle-Based Flow Cytometric Assays," *J. Immunol. Methods*, 243:243-255, 2000.

Wong et al., "Detection of Human Anti-Flavivirus Antibodies with a West Nile Virus Recombinant Antigen Microsphere Immunoassay," *J. Clin. Microbiol.*, vol. 42(1):65-72, 2004.

* cited by examiner

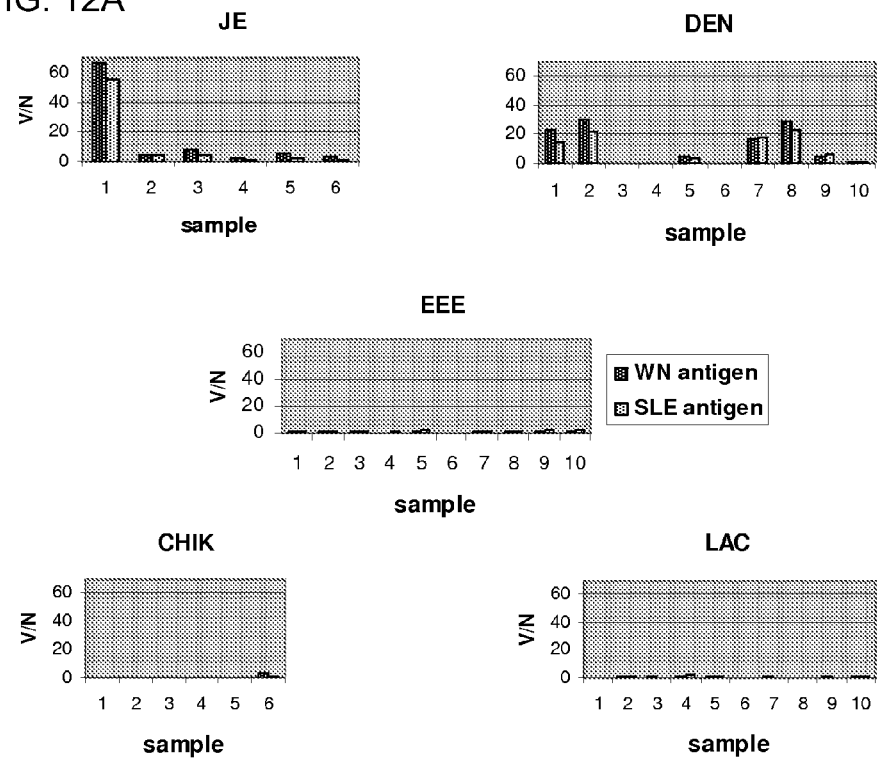
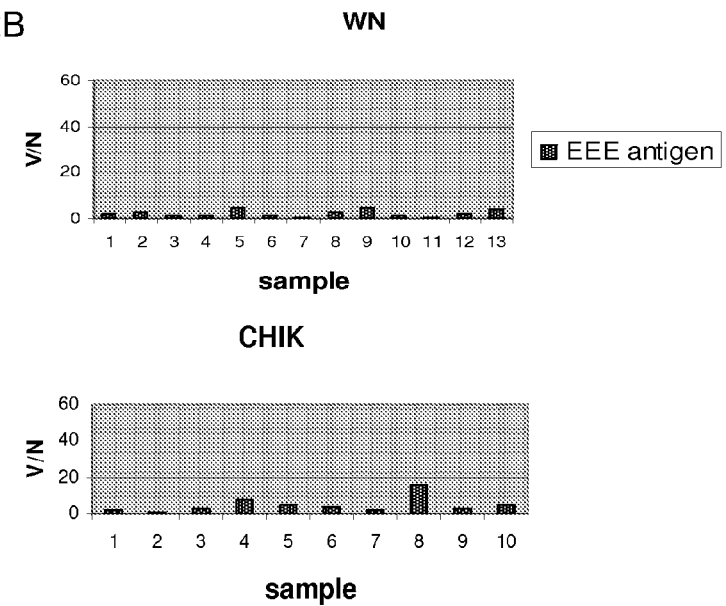

METHOD FOR DETECTION OF ANTIGEN-SPECIFIC ANTIBODIES IN BIOLOGICAL SAMPLES

CROSS REFERENCE TO RELATED APPLICATIONS

This application is the U.S. National Stage of International Application No. PCT/US2009/054916, filed Aug. 25, 2009, which was published in English under PCT Article 21(2), which in turn claims the benefit of U.S. Provisional Application No. 61/173,426, filed Apr. 28, 2009; U.S. Provisional Application No. 61/208,168, filed Feb. 19, 2009; and U.S. Provisional Application No. 61/093,605, filed Sep. 2, 2008. All of the above-referenced provisional applications are herein incorporated by reference in their entirety.

FIELD

This disclosure concerns direct labeling of biological samples to detect antigen-specific antibodies in samples obtained from any type of organism, such as human and veterinary subjects, plants, insects and bacteria.

BACKGROUND

Microsphere-based immunoassays (MIAs) are becoming increasingly popular for laboratory diagnosis of many diseases (Earley et al., *Cytometry* 50:239-242, 2002; Kellar et al., *Cytometry* 45:27-36, 2001). The technology involves the detection and analysis of a reaction (such as an antibody or other ligand) attached to microspheres or beads. The detecting instrument is a simplified flow cytometer, and lasers simultaneously identify the microsphere sets and measure the fluorescence associated with the reaction. The speed at which these tests can be performed and the ability to multiplex make this methodology particularly useful.

Limited methods exist for rapid identification of antigen-specific antibodies in animal species for which commercial secondary antibody conjugates and/or antisera are unavailable. The available assays are often of a complex nature, involving the use of live pathogens. Antisera (such as goat anti-alligator IgM) can be used to coat an ELISA plate or couple to a microsphere, followed by addition of serum, antigen and then antigen-specific conjugate. However antisera are available for a limited number of species, and the availability of species-specific secondary antibody is even more limited. This makes surveillance for antigen-specific antibodies in some species, such as wild avian species or zoo animals, cumbersome. A need remains to develop a rapid and safe assay for detection of antigen-specific antibodies that can be used for any species.

SUMMARY

Thus, provided herein is a microparticle-based assay system for direct labeling of biological samples (e.g., serum antibody), which alleviates the need for species-specific conjugates. By using this method for wild or exotic species, large numbers of samples can be screened. Furthermore, this assay format can be adapted for use with any number of etiologic agents of human or veterinary importance.

Disclosed herein is a rapid and universal assay for the detection of antigen-specific antibodies in biological samples, such as in serum, plasma or cerebral spinal fluid samples from human or veterinary subjects, insect blood meals, or protein extracts from transgenic plants or recombinant bacteria. The assay allows for the detection of antigen-specific antibodies in any species, including species for which secondary antibodies and/or antisera are not available. The disclosed assay can also be used as a total antibody test that detects all classes of antibodies simultaneously, instead of being limited to a particular antibody type. It is also possible to perform the assay in an unpurified sample that contains more than the target antibodies of interest, or more than just antibodies. For example, a serum sample or protein extract (such as a plant protein extract) can be subjected to the assay.

The disclosed assay provides a method for detecting antigen-specific antibodies of interest in a biological sample, wherein the antigen-specific antibodies of interest specifically bind to an antigen of interest. The method includes (i) providing a modified biological sample that is suspected of containing antibodies of interest specific for the antigen of interest, and may contain antibodies that bind to other than the antigen of interest. The biological sample has been modified by exposing it to a labeling agent that labels antibodies that are present in the biological sample (which may include the antibody of interest and other antibodies as well); (ii) contacting target antigen-bound microparticles with the modified biological sample, wherein the target antigen bound-microparticles bind antigen-specific antibodies to form labeled microparticle complexes if the antigen-specific antibodies are present in the biological sample; and (iii) detecting the labeled microparticle complexes. An increase in detection of the labeled microparticle complexes relative to a reference standard, such as control microparticle complexes, indicates the biological sample contains antigen-specific antibodies.

In some embodiments of the method, the labeling agent comprises a first specific binding partner, wherein the first specific binding partner is capable of binding to a second specific binding partner that carries a detectable label. Detecting the microparticle complexes comprises exposing the microparticle complexes to the second specific binding partner that carries the detectable label and detecting a signal from the label if the antigen-specific antibodies are present in the biological sample. In some embodiments, the specific binding partners are biotin and avidin or streptavidin.

In particular non-limiting disclosed embodiments, the serum sample is exposed to a labeling agent, such as biotin, to biotinylate antibodies in the sample (such as the antibodies of interest that may be present in the sample that specifically bind to the antigen of interest). Other biological components of the sample may also be biotinylated at that time, and more than just the antibodies of interest (that bind the antigen of interest) may be biotinylated. The biotinylated antibodies are then exposed to a particle that binds target antigen (such as the target antigen bound to an antibody coupled to the particle), but the particle does not bind biotinylated antibodies that do not bind the target antigen. Biotinylated antibodies that bind to the target antigen (which is in turn coupled to the particle) are detected by exposing them to a streptavidin or avidin linked detectable label to form a particle complex that is then detected by detection of the streptavidin linked detectable label.

Also provided herein are labeled microparticle complexes and compositions comprising the labeled microparticle complexes. The labeled microparticle complexes include (i) a target antigen-bound microparticle; (ii) an antibody that specifically binds the target antigen, wherein the antibody is conjugated to a first specific binding partner; and (iii) a second specific binding partner that carriers a detectable label.

In some other specific non-limiting examples, the sample is partially purified prior to labeling, for example to remove material (such as proteins) smaller than a target size, for example by passing the sample through an exclusion filter that removes material with a molecular weight less than 250 KDa or 100 KDa.

The foregoing and other features and advantages will become more apparent from the following detailed description of several embodiments which proceeds with reference to the accompanying figures.

BRIEF DESCRIPTION OF THE FIGURES

FIGS. 12A and 12B are a series of graphs showing cross-reactivity of the WN/SLE biotin-MIA (A) and EEE biotin-MIA (B) with antisera to other confirmed arboviral infections. The cut-off for a positive reaction was a V/N of 10.0 for WN; 10.23 for SLE; and 8.97 for EEE.

DETAILED DESCRIPTION

I. Abbreviations

Figure 1:
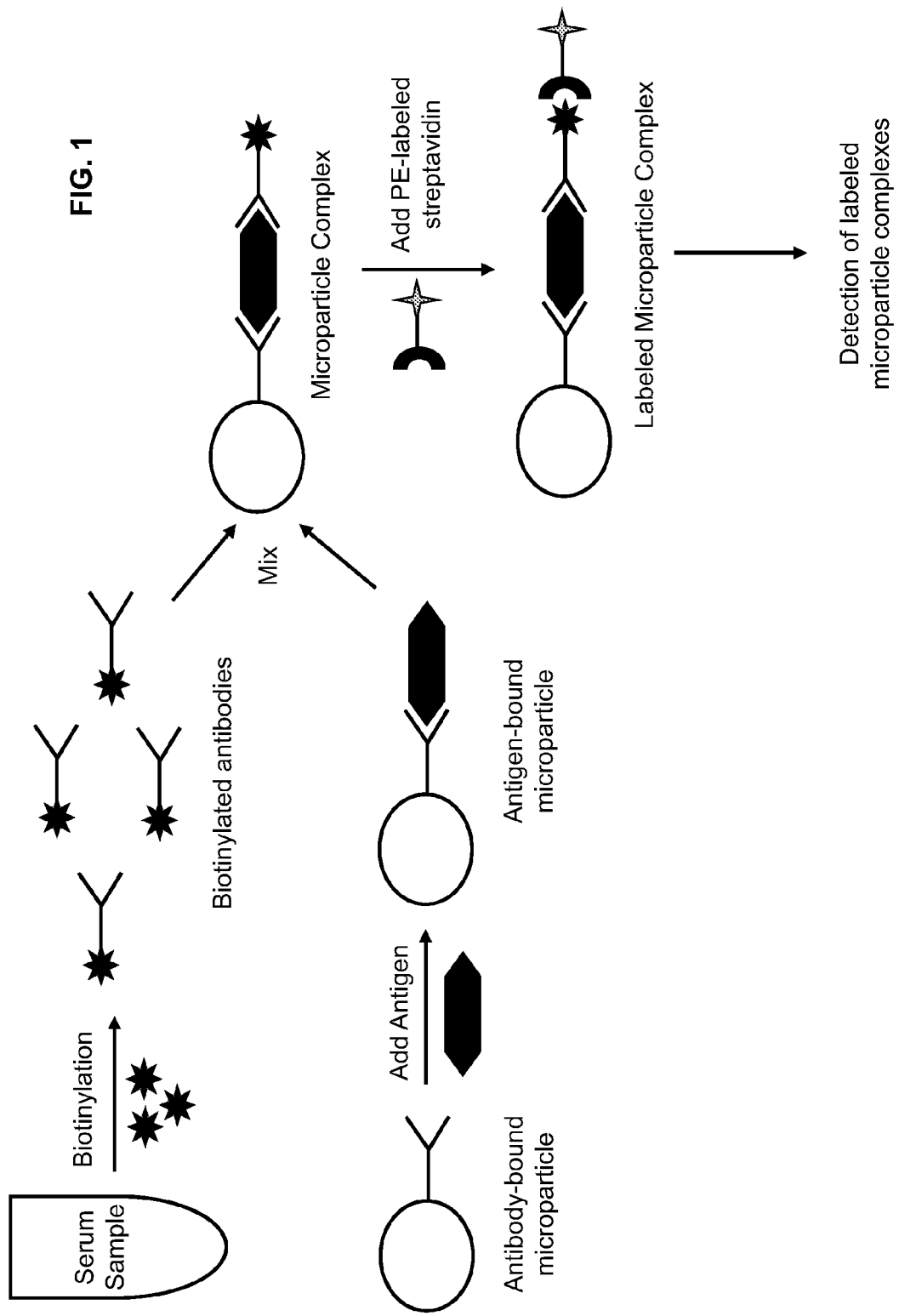
FIG. 1 is a schematic drawing showing a method of using first and second specific binding partners to detect the presence of antigen-specific antibodies in a biological sample. In the illustrated example, antibodies present in serum samples are biotinylated. If antigen-specific antibodies are present in the serum sample, they will bind to target antigens bound to microparticles, which can in turn be detected by a streptavidin label.

AUC Area under the curve
BSA Bovine serum albumin
CHIK Chikungunya
CI Confidence interval
CSF Cerebral spinal fluid
DEN Dengue
EEE Eastern equine encephalitis
ELISA Enzyme-linked immunosorbent assay
JE Japanese encephalitis
LAC La Crosse encephalitis
LCB Low cross buffer
MAb Monoclonal antibody
MFI Median fluorescence intensity
MIA Microsphere-based immunoassay
OD Optical density
PBS Phosphate-buffered saline
PE Phycoerythrin
PRNT Plaque reduction neutralization test
ROC Receiver operator characteristic
SLE St. Louis encephalitis
V/N Viral antigen/negative antigen
WN West Nile II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure and provide a more comprehensive summary of the disclosed methods, the following information is provided:

Alphavirus: A genus of viruses belonging to the Togaviridae family. Alphaviruses are transmitted between species by arthropods (arbovirus). Alphaviruses include, for example, eastern equine encephalitis virus, western equine encephalitis virus, Venezuelan equine encephalitis virus, Ross River virus, Semliki Forest virus, Sindbis virus and Chikungunya virus.

Animal: Living multi-cellular vertebrate organisms, a category that includes, for example, mammals, birds and reptiles. The term mammal includes both human and non-human mammals. Similarly, the term "subject" includes both human and veterinary subjects, for example, humans, non-human primates, dogs, cats, horses, birds and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. In avian and reptilian species, IgY antibodies are equivalent to mammalian IgG.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

The structure of IgY antibodies is similar to the structure of mammalian IgG, with two heavy ("nu" chains; approximately 67-70 kDa) and two light chains (22-30 kDa). The molecular weight of an IgY molecule is about 180 kDa, but it often runs as a smear on gels due to the presence of about 3% carbohydrate. Heavy chains (H) of IgY antibodies are composed of four constant domains and one variable domain, which contains the antigen-binding site.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller ($K_d$) indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope.

Antibody of interest: Any antibody in a sample, such as a clinical sample, that is of interest. In some embodiments, that antibody of interest is an antibody that binds a target antigen of interest. Antibodies of interest include pathogen-specific antibodies (such as virus-specific antibodies, including flavivirus-specific antibodies).

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. As used herein, a "target antigen" is an antigen (including an epitope of the antigen) that specifically binds the antibody of interest. "Specific binding" does not require exclusive binding. The target antigen may be used as a capture antigen to identify antibodies of interest in a biological sample that specifically recognize the antigen. In some embodiments, the target antigen is an antigen from a pathogen. In some embodiments, the antigen is a recombinant antigen. In some embodiments, the antigen is obtained from a cell or tissue extract. An antigen need not be a full-length protein. Antigens contemplated for use include any immunogenic fragments of a protein, such as any antigens having at least one epitope that can be specifically bound by an antibody.

Antigen-bound microparticle: In the context of this disclosure, an antigen-bound microparticle is a microparticle to which an antigen (including an epitope of an antigen) is directly or indirectly bound. In some embodiments, the antigen-bound microparticle is a microparticle coupled to an antibody that binds the antigen, which is further bound to the antigen. In other embodiments, the antigen-bound microparticle is a microparticle with a covalently bound antigen.

Antigen-specific: As used herein, an "antigen-specific" antibody is an antibody that was elicited (produced and/or activated) in response to a particular antigen. An "antigen-specific" antibody is capable of binding to the antigen, typically with high affinity.

Arboviruses: Viruses that are transmitted by arthropods (arthropod-borne), such as mosquitoes and ticks. These viruses replicate in arthropods and are transmitted by biting a host. Arboviruses include, but are not limited to, members of the Togaviridae, Bunyaviridae, Flaviviridae and Arenaviridae families, such as Chikungunya virus, dengue virus, Ross River virus, vesicular stomatitis virus, West Nile virus, yellow fever virus, tick-borne encephalitis virus, Japanese encephalitis virus, La Crosse encephalitis virus, Murray Valley encephalitis virus, Rift Valley fever virus, St. Louis encephalitis virus and equine encephalitis viruses.

Avidin/Streptavidin: The extraordinary affinity of avidin for biotin allows biotin-containing molecules in a complex mixture to be discretely bound with avidin. Avidin is a glycoprotein found in the egg white and tissues of birds, reptiles and amphibia. It contains four identical subunits having a combined mass of 67,000-68,000 daltons. Each subunit consists of 128 amino acids and binds one molecule of biotin. Extensive chemical modification has little effect on the activity of avidin, making it especially useful for protein purification.

Another biotin-binding protein is streptavidin, which is isolated from *Streptomyces avidinii* and has a mass of 60,000 daltons. In contrast to avidin, streptavidin has no carbohydrate and has a mildly acidic pI of 5.5. Another version of avidin is NeutrAvidin Biotin Binding Protein (available from Pierce Biotechnology) with a mass of approximately 60,000 daltons.

The avidin-biotin complex is the strongest known non-covalent interaction ($Ka=10^{15}$ $M^{-1}$) between a protein and ligand. The bond formation between biotin and avidin is very rapid, and once formed, is unaffected by extremes of pH, temperature, organic solvents and other denaturing agents.

Although examples disclosed herein use streptavidin as a specific binding agent, the streptavidin could be substituted with other types of avidin. The term "avidin" is meant to refer to avidin, streptavidin and other forms of avidin (such as derivatives or analogs thereof) that have similar biotin binding characteristics. Analogs or derivatives of avidin/streptavidin include, but are not limited to, nitro-streptavidin, non-glycosylated avidin, N-acyl avidins (such as N-acetyl, N-phthalyl and N-succinyl avidin), and the commercial products ExtrAvidin™ (Sigma-Aldrich), Neutralite Avidin (SouthernBiotech) and CaptAvidin (Invitrogen). Additional avidin/streptavidin analogs and derivatives are known in the art (see, for example, U.S. Pat. No. 5,973,124 and U.S. Patent Application Publication Nos. US 2004/0191832; US 2007/0105162; and US 2008/0255004).

Biological sample: As used herein, a "biological sample" refers to a sample obtained from a subject (such as a human or veterinary subject) or other type of organism, such as a plant, bacteria or insect. In particular examples of the method disclosed herein, the biological sample is a fluid sample. Biological samples from a subject include, but are not limited to, serum, blood, plasma, urine, saliva, cerebral spinal fluid (CSF) or other bodily fluid. Biological samples can also refer to cells or tissue samples. In some cases, the biological sample is from a plant (for example, a plant engineered to express an antibody), such as a protein extract from a plant or plant material. Biological samples also include extracts (such as protein extracts) from bacteria, such as bacteria than have been modified to produce a protein (e.g., an antibody) of interest. In other examples, the biological sample is from an insect, such as a vector blood meal. As used herein, a "modified biological sample" is a biological sample that has been exposed to a labeling agent. In some embodiments, the labeling agent labels antibodies that are present in the biological sample.

Biotin: A molecule (also known as vitamin H or vitamin $B_7$) that binds with high affinity to avidin and streptavidin. Biotin is often used to label nucleic acids and proteins for subsequent detection by avidin or streptavidin linked to a detectable label, such as a fluorescent or enzymatic reporter molecule. Biotinylation of a molecule (such as an antibody or other protein sample) is routinely achieved in the art by reacting a free carboxyl group on biotin with an amine group on a protein, such as an amine group found in an antibody or protein analyte/analog. Unless indicated otherwise, the term "biotin" includes derivatives or analogs that participate in a binding reaction with avidin. Biotin analogs and derivatives include, but are not limited to, N-hydroxysuccinimide-iminobiotin (NHS-iminobiotin), amino or sulfhydryl derivatives of 2-iminobiotin, amidobiotin, desthiobiotin, biotin sulfone, caproylamidobiotin and biocytin, biotinyl-ϵ-aminocaproic acid-N-hydroxysuccinimide ester, sulfo-succinimide-iminobiotin, biotinbromoacetylhydrazide, p-diazobenzoyl biocytin, 3-(N-maleimidopropionyl) biocytin, 6-(6-biotinamidohexanamido)hexanoate and 2-biotinamidoethanethiol. Biotin derivatives are also commercially available, such as DSB-X™ Biotin (Invitrogen). Additional biotin analogs and derivatives are known in the art (see, for example, U.S. Pat. No. 5,168,049; U.S. Patent Application Publication Nos. 2004/0024197, 2001/0016343, and 2005/0048012; and PCT Publication No. WO 1995/007466). The use of biotin is well-documented to make secondary antibodies or other limited uses, but the use described in this specification is to screen a biological sample, such as an unpurified biological sample.

Biotin binding protein: A protein that binds biotin with sufficiently great affinity for an intended purpose. Examples of biotin binding proteins are well known in the art, and include avidin, streptavidin, NeutrAvidin, and monoclonal antibodies or receptor molecules that specifically bind biotin. In the context of this disclosure, streptavidin could be replaced with any other biotin-binding proteins, or a combination of biotin binding proteins.

Blood meal: Refers to the stomach contents of a blood-sucking insect.

Conjugated: Refers to two molecules that are bonded together, for example by covalent bonds. An example of a conjugate is a molecule (such as avidin/streptavidin) conjugated to a detectable label, such as a fluorophore, to form a detection substrate.

Contacting: Placement in direct physical association; includes both in solid and liquid form. As used herein, "contacting" is used interchangeably with "exposed."

Control: A reference standard, for example a positive control or negative control. A positive control is known to provide a positive test result. A negative control is known to provide a negative test result. However, the reference standard can be a theoretical or computed result, for example a result obtained in a population.

Engineered antibody: Any non-naturally occurring antibody, such as an antibody produced by recombinant means.

Epitope: An antigenic determinant. Epitopes are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Flavivirus: A genus of viruses which are transmitted by the bite of infected arthropods (e.g., ticks or mosquitoes). Flaviviruses are enveloped viruses with a positive-sense single-stranded RNA genome. Many members of the flavivirus genus cause encephalitis in animal (including human) hosts. Flaviviruses include, but are not limited to, West Nile virus, St. Louis encephalitis virus, Japanese encephalitis virus, yellow fever virus, dengue virus, Murray Valley encephalitis virus and Powassan virus.

Flow instrument: Includes any instrument that analyzes individual particles in a fluid mixture based on the particle's characteristics, such as size.

Fluorophore: A chemical compound, which when excited by exposure to a particular wavelength of light, emits light (i.e., fluoresces), for example at a different wavelength.

Examples of fluorophores that may be used in the methods disclosed herein are provided in U.S. Pat. No. 5,866,366 to Nazarenko et al.: 4-acetamido-4'-isothiocyanatostilbene-2, 2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999).

Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art may also be used, for example those available from Molecular Probes (Eugene, Oreg.).

Immunogenic peptide: A peptide which comprises a specific motif (or other sequence) such that the peptide will bind an MHC molecule and induce a cytotoxic T lymphocyte (CTL) response, or a B cell response (e.g. antibody production) against the antigen from which the immunogenic peptide is derived. Also referred to herein as an "immunogenic fragment" (i.e. an immunogenic portion of a peptide).

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A label is an agent placed on a target to directly or indirectly render it detectable. Hence the label can be a component applied to the target that subsequently binds a detectable agent. A "detectable label" is a detectable compound or composition that is conjugated directly or indirectly to another molecule, such as an antibody or a protein, to facilitate detection of that molecule. Specific, non-limiting examples of detectable labels include fluorescent tags, enzymatic linkages, and radioactive isotopes. In some embodiments, the detectable label is a detectable marker conjugated to a biotin-binding agent, such as avidin or streptavidin (for example, streptavidin conjugated to a fluorescent marker or enzymatic activity that can be detected by optical or colorimetric methods). "Labeling" refers to the act of linking a label to a molecule of interest, for example linking to the molecule of interest a component that subsequently binds a detectable label or linking a detectable label itself to the molecule of interest, or both. Various methods of labeling polypeptides and other molecules are known in the art and may be used. Examples of detectable labels for polypeptides include, but are not limited to, the following: radioisotopes or radionucleotides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, chromophores (such as horseradish peroxidase or alkaline phosphatase), biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates.

Labeling agent: In the context of the present disclosure, a "labeling agent" is a compound or other agent that can be used to label a molecule or molecules of interest, such as proteins, including antibodies. The labeling agent need not itself carry a detectable moiety, but may instead be a component that is subsequently used to bind a detectable label. In some embodiments, the labeling agent comprises a first specific binding partner that does not itself provide a detectable signal for subsequent detection. The first specific binding partner, which labels the molecule of interest, is capable of binding a second specific binding partner that includes a detectable label. In particular examples, the first specific binding partner is biotin and the second specific binding partner is avidin or streptavidin that carries a detectable label.

Livestock: Domesticated animals reared in an agricultural setting as a source of food or to provide labor. The term "livestock" includes, but is not limited to, cattle, deer, donkeys, goats, horses, mules, rabbits and sheep.

Microparticle: A particle that is generally about 0.01 to about 1000 microns in diameter. Microparticles include microspheres (spherical microparticles), beads, or the like with a surface suitable for binding (e.g., suitable for binding an antibody). For example, a microparticle can be a microsphere with a carboxylated surface. In some embodiments, the microparticles are polymeric microparticles (a microparticle made up of repeating subunits of a particular substance or substances). In some examples, the polymeric microparticles are polystyrene microparticles, such as a polystyrene microparticle with a carboxylated surface. In other examples, the microparticles are magnetic beads. Suitable magnetic beads are well known in the art and include, but are not limited to, functional magnetic beads (e.g., beads of 1 or 5 microns) from Bioclone Inc. (San Diego, Calif.) or Dynal™ Dynabeads™ (Invitrogen, Carlsbad, Calif.). Microspheres or beads for use in flow cytometry and flow instrumentation are well known in the art and are commercially available from a variety of sources.

Microparticle complex: In the context of the present disclosure, a "microparticle complex" is a bound complex comprising an antigen-bound microparticle, and an antibody that specifically binds the target antigen. The antibody is further bound or conjugated to a first specific binding partner (such as biotin). As used herein, a "labeled microparticle complex" is a microparticle complex that further includes a second specific binding partner (such as avidin) that can be conjugated to a detectable label (such as a fluorophore). A "detectably labeled microparticle complex" is a microparticle complex that further includes a second specific binding partner (such as avidin) that is conjugated to a detectable label (such as a fluorophore). As used herein, a "target antigen-bound microparticle" is a microparticle that is bound to an antigen. The target antigen can be directly conjugated to the microparticle, or the microparticle can be directly conjugated to an antibody that specifically binds the target antigen.

Morbillivirus: A genus of viruses that belong to the Paramyxoviridae family. Morbilliviruses include, but are not limited to, measles virus, canine distemper virus and rinderpest virus.

Negative control antigen: An antigen that is not reactive with an antibody of interest.

Negative control serum: Serum in which antibodies of interest are not present in the serum. A negative control serum can be used as a control in an experimental study or assay to confirm that other reactions are not affecting the experimental or assay results obtained on the samples. Any positive results of reactivity using a negative control serum would be cause for concern about the quality of the experimental or assay results.

Pathogen: A biological agent that causes disease or illness to its host. Pathogens include, for example, bacteria, viruses, fungi, protozoa and parasites. Pathogens are also referred to as infectious agents. The pathogen typically includes the target antigen that is to be detected by the disclosed methods.

Examples of such pathogenic viruses include, but are not limited to those in the following virus families: Retroviridae (for example, human immunodeficiency virus (HIV), human T-cell leukemia viruses; Picornaviridae (for example, polio virus, hepatitis A virus, hepatitis C virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus), rubella viruses); Flaviridae (for example, dengue viruses, yellow fever viruses, West Nile virus, St. Louis encephalitis virus, Japanese encephalitis virus, Powassan virus and other encephalitis viruses); Coronaviridae (for example, coronaviruses, severe acute respiratory syndrome (SARS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, respiratory syncytial virus; also includes morbilliviruses, such as measles virus, rinderpest virus and canine distemper virus); Orthomyxoviridae (for example, influenza viruses, including avian influenza and swine influenza, for example swine influenza A (H1N1)); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; and other herpes viruses, including HSV-6); Poxyiridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus). In some embodiments, the pathogen is an arbovirus.

Examples of such bacterial pathogens include, but are not limited to: *Helicobacter pylori, Escherichia coli, Vibrio cholerae, Borrelia burgdorferi, Legionella pneumophilia, Mycobacteria* sps (such as *M. tuberculosis, M. avium, M. intracellulare, M. kansaii, M. gordonae), Staphylococcus aureus, Neisseria gonorrhoeae, Neisseria meningitidis, Listeria monocytogenes, Coxiella burnetii, Yersinia pestis, Francisella tularensis, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelli*.

Examples of such fungal pathogens include, but are not limited to: *Cryptococcus neoformans, Histoplasma capsulatum, Coccidioides immitis, Blastomyces dermatitidis, Chlamydia trachomatis, Candida albicans*.

Other pathogens (such as parasitic pathogens) include, but are not limited to: *Plasmodium falciparum, Plasmodium vivax, Trypanosoma cruzi* and *Toxoplasma gondii*.

Positive control: This can be a serum in which known antibodies of interest are present. A positive control serum can be used as a control in an experimental study or assay to confirm reactivity between antigens and the antibodies tested for in a sample. Reaction rates between specific viral antigens and the antibodies tested for in a sample can differ and the use of positive control serum allows for quantification of such differences for data standardization purposes. The positive control can also be an antibody, such as a monoclonal antibody specific for the antigen of interest, or an engineered antibody such as a humanized mouse monoclonal antibody. Positive controls are primarily used to ascertain that all the other test components are working correctly.

Purified: The term purified does not require absolute purity; rather, it is intended as a relative term. Thus, for example, a purified peptide preparation is one in which the peptide or protein is more enriched than the peptide or protein is in its natural environment within a cell. The samples disclosed herein may be unpurified or partially purified, for example by preparing a protein extract from a plant or obtaining the serum component of blood. However, the sample need not be purified to remove all but the antibodies in the sample. It has also been found, in some other specific non-limiting examples, that test results can be improved by partially purifying the sample (for example following labeling, for example following biotinylation). In some examples, the purification removes material (such as proteins) smaller than a target size, for example smaller than the size of antibodies that are to be labeled. In some examples, the sample is partially purified by placing it through an exclusion filter that removes material smaller than 500 KDa, for example smaller than 250 KDa or 100 KDa. For example, a size exclusion filter can be used to substantially remove much smaller and untargeted biotinylated proteins (such as albumin). In other examples, the sample is a protein extract such as a protein extract from a plant. In other examples, the sample is the serum portion of the blood.

Reactive microparticle: Refers to any microparticle to which a reactive molecule is bound. For example, a microparticle with a covalently bound antibody is a reactive microparticle.

Serum: The fluid portion of the blood that separates out from clotted blood. Serum contains many proteins, including antibodies, but does not contain clotting factors.

Specific binding partner: A member of a pair of molecules that interact by means of specific, non-covalent interactions that depend on the three-dimensional structures of the molecules involved. Exemplary pairs of specific binding partners include antigen/antibody, hapten/antibody, ligand/receptor, nucleic acid strand/complementary nucleic acid strand, substrate/enzyme, inhibitor/enzyme, carbohydrate/lectin, biotin/avidin (such as biotin/streptavidin), and virus/cellular receptor.

Viral group-reactive antibody: Refers to any antibody that is reactive to a plurality of viral antigens (e.g., a plurality of virus types) within the same viral group. For example, a flavivirus group-reactive antibody such as the monoclonal antibody (MAb) 6B6C-1 is reactive with viral antigens from the flavivirus genus, which includes West Nile virus, Saint Louis encephalitis virus, Japanese encephalitis virus, Murray Valley encephalitis virus, yellow fever virus and dengue virus.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Method for Detection of Antigen-Specific Antibodies

Described herein is a system for labeling (such as by biotinylation) of biological samples that alleviates the need for species-specific conjugates for detection of antigen-specific antibodies. In some examples, the method involves labeling (for example by biotinylation) of the free amines in biological samples (such as serum samples), which can be obtained from a variety of mammalian, reptilian and/or avian species. In one example disclosed herein, biotinylated serum samples were size-filtered (100 kDa molecular weight cutoff) in a 96-well format to remove unwanted molecules, such as excess biotin and small molecular weight components, such as serum albumin (AcroPrep™ 100, Pall Corporation, East Hills, N.Y.). The biotinylated antibodies in the sample were captured by target antigens (for example, West Nile and St. Louis encephalitis virus antigens) in a microparticle assay. Antigen-specific antibodies bound to the microparticle complex were detected using streptavidin-phycoerythrin (PE) to bind the biotinylated antibodies present in the serum sample. The results reflect total antigen-specific antibody content.

As described herein, serum samples collected from multiple wild and domestic species, including wild-caught birds, mammals, reptiles and humans, were assayed for antibodies to West Nile virus, St. Louis encephalitis virus and eastern equine encephalitis virus. Results were compared to those obtained using confirmatory tests. The infecting virus could reliably be identified in most species using this method. This method can be used alone to identify antigen-specific antibodies in serum samples, or in combination with an alternate test (such as a blocking ELISA) or confirmatory test (such as PRNT), thus reducing the volume of confirmatory testing required. By using this method for wild or exotic species, large numbers of samples can be screened. Furthermore, this method is adaptable for use with other etiologic agents of human and veterinary importance, as well as for detection of engineered antibodies, such as from plants or recombinant microorganisms.

Provided herein is a method for detecting antigen-specific antibodies in a biological sample, wherein the antigen-specific antibodies specifically bind to a target antigen. In some embodiments, the method includes (i) providing a modified biological sample that is suspected of containing antibodies specific for the target antigen, wherein the biological sample has been modified by exposing it to a labeling agent that labels antibodies that are present in the biological sample; (ii) contacting target antigen-bound microparticles with the modified biological sample, wherein the target antigen bound-microparticles bind antigen-specific antibodies to form labeled microparticle complexes if the antigen-specific antibodies are present in the biological sample; and (iii) detecting the labeled microparticle complexes, wherein an increase in detection of the labeled microparticle complexes relative to a reference standard, such as control detectable microparticle complexes, indicates the biological sample contains antigen-specific antibodies. The labeled microparticle complexes may be formed, for example, by linking the microparticle complex to a detectable label either before or after the antigen-specific antibodies bind the target antigen bound-microparticles. The reference standard can be, for example, a negative control or a result expected from a negative control, such as a reduced or substantially absent formation of labeled microparticle complexes. In some examples, the negative control is a microparticle complex comprising a control antigen-bound microparticle. The control microparticle complexes are contacted with the modified biological sample as in step (ii), but should not bind the labeled antibodies in the modified biological sample.

In some embodiments of the method, the labeling agent comprises a first specific binding partner, wherein the first specific binding partner is capable of binding to a second specific binding partner that carries a detectable label. Detecting the microparticle complexes includes exposing the microparticle complexes to the second specific binding partner that carries the detectable label and detecting a signal from the label if the antigen-specific antibodies are present in the biological sample.

In some examples, the first and second specific binding partners are selected from the group consisting of avidin and biotin. For example, in some cases the first specific binding partner is biotin and the second specific binding partner is avidin. In some embodiments, providing a modified biological sample comprises biotinylating the biological sample.

Although the use of biotin is exemplified herein as a means to directly label antibodies in a biological sample, any molecule that attaches to amino or carboxyl groups is contemplated for use with the methods provided herein. Useful molecules include any molecules that have a corresponding binding partner that can be conjugated to a detectable label or that is directly detectable. Methods of biotinylation are well known in the art (see, for example, Peränen, *Biotechniques* 13(4):546-549, 1992; Strachan et al., *J. Mol. Recognit.* 17(3): 268-276, 2004; Mao, 1999, "Biotinylation of Antibodies," From Methods in Molecular Biology, vol. 115, pages 39-41, Immunocytochemical Methods and Protocols, edited by Lorette C. Javois, Humana Press, Tolowa, N.J.) and exemplary methods are provided in Example 1 and Example 2 below. In addition, kits for biotinylation of proteins are commercially available.

In some embodiments, the target antigen-bound microparticles comprise the target antigen bound to an antibody that binds the target antigen, and a microparticle coupled to the antibody (see FIG. 1). In other embodiments, the target antigen-bound microparticles comprise a microparticle covalently bound to the target antigen, for example by a linker molecule.

In some embodiments, the biological sample is a bodily fluid sample from a human or veterinary subject, such as a serum sample, blood sample, plasma sample, urine sample or CSF sample. In particular examples, the biological sample is a serum sample.

In some embodiments, the biological sample is obtained from a mammalian species. In some examples, the mammalian species is a primate, such as a human. In other examples, the mammalian species is a black bear, horse, cat, dog or squirrel. In other embodiments, the biological sample is obtained from a reptilian species, such as an alligator. In other embodiments, the biological sample is obtained from an avian species. In some examples, the avian species is an American kestrel, great horned owl, common barn owl, red-tailed hawk, Swainson's hawk, eastern screech owl, golden eagle, red-winged blackbird, chicken, house sparrow, cliff swallow, American crow, great egret, rock pigeon, grackle, European starling, great blue heron, pheasant, ferruginous hawk, long-eared owl, prairie falcon, bald eagle, rough-legged hawk, burrowing owl or turkey vulture.

In some embodiments, the biological sample is from an insect (for example, a mosquito, lice, fly, gnat etc.), such as a vector blood meal.

In other embodiments, the biological sample is from a plant. The biological sample can be, for example, a protein extract from a plant or plant material, such as leaves. In some examples, the plant is engineered to express an antibody that specifically recognizes a plant pathogen. In other examples, the plant is engineered to express an antibody specific for a non-plant pathogen, such as a human or veterinary pathogen. Such antibodies can be produced in plants for diagnostic or therapeutic purposes.

The target antigen can be any type of antigen, such as an antigen (including an epitope or other immunogenic peptide) from a pathogen. A list of such pathogens has been provided earlier in this specification. In some embodiments, the pathogen is a bacterial pathogen. In particular examples, the bacterial pathogen is *Coxiella burnetii, Yersinia pestis, Borrelia burgdorferi, Francisella tularensis*, or a *Mycobacterium* species. *Mycobacterium* species include, but are not limited to, *M. tuberculosis, M. avium, M. intracellulare, M. kansaii* and *M. gordonae*. In some embodiments, the pathogen is a parasite. In one example, the parasite is *Toxoplasma gondii*. In other embodiments, the pathogen is a virus, such as avian influenza, swine influenza, an arbovirus or a morbillivirus. In some examples, the morbillivirus is measles virus, rinderpest virus or canine distemper virus. In other examples, the arbovirus is a flavivirus or an alphavirus. Flaviviruses include, but are not limited to, West Nile virus, St. Louis encephalitis virus, yellow fever virus, dengue virus, Japanese encephalitis virus and Murray Valley encephalitis virus. In some embodiments, the virus is an alphavirus. In some examples, the alphavirus is eastern equine encephalitis virus. In some embodiments, the pathogen is a plant pathogen, such as a plant virus. The antigen from a pathogen can be any antigenic protein from the pathogen, or an immunogenic fragment of the antigenic protein.

In some embodiments wherein the target antigen is from a flavivirus, the target antigen is the flavivirus prM-E protein.

In some embodiments, the microparticles are microspheres. In particular embodiments, the microspheres are polystyrene microspheres, such as carboxylated microspheres. However, other shapes for the microparticles are known in the art. In some cases, the microparticles are about 1 to about 100 microns in diameter. In some examples, the microparticles are about 2.5 to about 10 microns in diameter. In other embodiments, the microparticles are magnetic beads.

The label bound to the second specific binding partner can be any type of detectable label suitable for use with the methods provided herein. In some embodiments, the label is a fluorophore. In some examples, the fluorophore is phycoerythrin, fluorescein isothiocyanate or rhodamine. Examples of additional suitable fluorophores are well known in the art.

In some embodiments, the microparticles are detected using a flow instrument, such as a flow cytometer. In other embodiments, the microparticles are detected using a plate-based immunoassay, such as an enzyme-linked immunosorbent assay (ELISA). When the microparticles are microspheres, the preferred assay format uses a flow instrument for detection. However, plate-based assays are also contemplated.

In some embodiments, a positive or negative result is determined by comparison to a reference standard, such as a control sample. In some examples, the control sample is generated by contacting antibody-coupled microparticles to a control antigen. In other examples, the control sample is generated by contacting biotinylated negative control serum with target antigen-bound microparticles and a biotin binding partner conjugated to a label. In other embodiments, the reference standard is a result obtained from the control sample, or multiple control samples, such as a numerical value.

In some embodiments of the methods provided herein, the method further comprises performing an alternate or confirmatory test, such as a plate-based immunological assay, for example, an ELISA (including antibody-blocking ELISA), or a plaque-reduction neutralization test (PRNT).

Also provided herein is a labeled microparticle complex, wherein the complex comprises (i) a target antigen-bound microparticle; (ii) an antibody that specifically binds the target antigen, wherein the antibody is conjugated to the first specific binding partner; and (iii) a second specific binding partner that carries a detectable label (which is a variation of the method shown in FIG. 1). As described herein, the target antigen-bound microparticle comprises the target antigen bound to an antibody that is coupled to a microparticle. In some embodiments, the specific binding partners are avidin and biotin. In some embodiments, the detectable label is a fluorophore. Compositions comprising the disclosed labeled microparticle complexes are also provided.

The biotin microparticle-based immunoassay disclosed herein has several advantages over previously described techniques to detect antigen-specific antibodies in serum samples. In comparison with an antibody-blocking ELISA (see, for example, Blitvich et al., *J. Clin. Microbiol.* 41(6):2676-2679, 2003), the method provided herein is less complex, more rapid, requires very small sample volumes and can detect agent-specific total antibody content in serum samples regardless of the species of origin. In addition, many prior assays (see, for example, Bossart et al., *J. Virol. Methods.* 142(1-2):29-40, 2007) require the use of secondary antibodies or protein A/G to bind the antibody of interest in the serum sample. However, secondary antibodies are not commercially available or routine to generate for all species, and protein A/G does not bind antibodies from all species, such as reptilian and avian species (which have IgY antibodies in place of IgG). Therefore, prior methods are limited to those species for which secondary antibodies are commercially available and/or species which have antibodies that bind protein A/G. The present method can be performed without the use of a secondary antibody or protein A/G to bind the antigen of interest in the serum sample. PRNTs are often the gold standard confirmatory assay but are technically challenging, very time-consuming, require the use of live pathogens and are expensive.

Furthermore, in some examples described herein the method uses a microparticle coupled to an antibody as a means of binding the target antigen. Any assays that use secondary antibodies or protein A/G would not work with a method utilizing microparticles coupled to an antibody if the secondary antibody is of the same species as the capture antibody. The advantage of using antibody-coupled microparticles is that the target antigen need not be completely pure. In addition, some antigens are not amenable to direct attachment to a microparticle. The use of microspheres in the provided method is further advantageous over a plate-based assay format because the latter format results in greater non-specific binding.

The microsphere-based assay format is especially suited to detect infection in animals that serve as reservoirs for zoonotic pathogens. The ability of the disclosed MIA to simultaneously detect all antibody isotypes is an advantage for surveillance applications because the timing of infection is rarely known. Concentrations of IgG can be assumed to be greater than IgM in many samples, especially those that were not obtained in the acute phase of an infection. As described herein, the assay disclosed herein gives accurate results with randomly-timed samples and is capable of detecting IgM in biological samples.

The assay disclosed herein represents the first demonstration of a single platform species-independent rapid test that directly detects the antibodies of interest with high accuracy and sensitivity.

IV. Detection of Pathogen-Specific Engineered Antibodies in Plants

The methods of detecting antigen-specific antibodies in a biological sample disclosed herein can be used to identify the presence of engineered antibodies in other organisms, such as plants. Antibody or antibody fragments can be expressed in plants for the purpose of protecting the plant against plant pathogens, such as viruses, or to synthesize large quantities of antibodies for diagnostic or therapeutic purposes (De Jaeger et al., *Plant Mol. Biol.* 43:419-428, 2000; Di Carli et al., *J. Proteome Res.* 8:838-848, 2009). In the latter case, the engineered antibodies can be specific for any target antigen of interest, including antigens from human pathogens.

In some embodiments, to detect antigen-specific antibodies in plants, a protein extract is prepared from the plant or plant material (such as the leaves) according to standard procedures. Exemplary extraction procedures are provided in Example 3 below. The extract (i.e. the biological sample) is modified by exposing it to a labeling agent that labels antibodies that are present in the biological sample. The modified biological sample is contacted with target antigen-bound microparticles to form labeled microparticle complexes if the antigen-specific antibodies are present in the biological sample. The labeled microparticle complexes are detected as described herein. An increase in detection of the labeled microparticle complexes relative to a reference standard, such as control microparticle complexes, indicates the biological sample (the plant extract) contains antigen-specific antibodies.

This method also can be applied to other organisms (such as bacteria) that express recombinant or engineered antibodies or antibody fragments. As described above, a protein extract is prepared from the organism and modified with a labeling agent to generate a modified biological sample. The modified biological sample is used according to the methods described herein to detect the presence of antigen-specific antibodies in the organism.

V. Microparticle Assays

The methods of the present disclosure may be carried out with one or more different antigen-bound microparticles. The number of different types of antigen-bound microparticles can vary depending on the number of different types of antigen-specific antibodies to be screened for in the biological sample. In some embodiments, a plurality of antigen-bound microparticles is used to detect antibodies to a plurality of pathogens within a sample concurrently. By "concurrently" or "simultaneously," it is meant that the presence of a plurality of pathogen-specific antibodies present in a sample can be detected in a single experimental protocol.

Microparticles for use in the disclosed methods can be any particle or bead to which antigens can be directed attached, or to which an antibody can be directly attached. Suitable particles can be analyzed using a flow instrument, such as a flow cytometer. In some embodiments, the microparticles are microspheres. In particular examples, the microsphere has a carboxylated surface. In some embodiments, the microparticles are magnetic beads. Microparticles that can be used with the present disclosure are available commercially from several companies including Luminex Corp. (Austin, Tex.), Bioclone Inc. (San Diego, Calif.), Invitrogen (Carlsbad, Calif.) and Becton Dickinson (San Jose, Calif.). Microparticles preferably range in size from about 0.01 to 1000 µM in diameter. In some examples, the microparticles are about 1 µM to about 20 µM in diameter.

Microparticles within a single microparticle set (microparticles bound to the same antigen) are preferably about the same size. Beads from different microparticle sets (microparticles bound to different antigens) can be of the same size or can vary in size so that their size can serve as a distinguishing parameter or unique sorting characteristic for use in the methods of the present disclosure. Microparticle sets comprising microparticles of about the same size may be distinguished based on another parameter, such as a unique spectral property (for example, bound to a different fluorophore), which may be detected by a flow instrument.

The microparticles can be constructed of any material to which antigens or antibodies can be conjugated. For example, materials for the construction of microparticles include, but are not limited to: polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, or combinations thereof.

Microparticles can optionally comprise additional functional groups useful for attachment of antibodies or antigens. Such functional groups include, but are not limited to, carboxylates, esters, alcohols, carbamides, aldehydes, amines, sulfur oxides, nitrogen oxides, or halides. Microparticles comprising such functional groups are available commercially. For example, Luminex provides carboxylated microspheres. Carboxylation of the microspheres permits the covalent coupling of proteins using straightforward chemical techniques.

Any characteristic or parameter capable of being detected and/or quantified by a flow cytometer or other detection instrument can provide a basis for particle selection or sorting by a detection instrument. The parameters provide a means for distinguishing one microparticle complex from another, thus multiple antigen-specific antibodies within a sample can be separately detected. In some embodiments, the unique sorting characteristic that defines the microparticle complexes is a unique spectral property, such as the presence of a different fluorophore.

In the context of the present disclosure, the labeled microparticle complex can be labeled with any molecule capable of being detected by a flow instrument or other detection instrument, such as a fluorescent label. In some embodiments, suitable fluorescent labels emit light within the range detectable by the flow instrument. Instruments for use in the disclosed methods comprise a method of excitation, such as a laser, which have a known excitation wavelength that dictates the necessary emission wavelength of the fluorescent label. For example, the LUMINEX100™ (Luminex, Austin, Tex.) detection instrument comprises an argon laser, which has an excitation wavelength of 532 nm. Based on this excitation wavelength, in order to use the LUMINEX100™ with the disclosed methods, one must choose a fluorescent label that emits light at or near 575 nm. Varying the method of excitation, therefore, will allow the use of a greater variety of fluorescent labels.

In some embodiments of the disclosure, the microparticle complexes are labeled with a fluorophore. One of skill in the art will recognize that any fluorescent molecule capable of being detected and/or quantified by the detection instrument can be used to label the microparticle complexes of the present disclosure. As discussed above, the means of excitation and the detection means of the detection instrument will dictate the choice of available fluorophore. Fluorescent molecules include, but are not limited to: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999). Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800, 996 to Lee et al.) and derivatives thereof. Other fluorophores known to those skilled in the art may also be used, for example those available from Molecular Probes (Eugene, Oreg.). Additional fluorescent molecules that can be used in conjunction with the methods of the present disclosure are well known in the art (see, for example, Shapiro, Practical Flow Cytometry, Third edition. New York: Wiley-Liss, 1995).

In one embodiment of the present disclosure, the presence of pathogen-specific antibodies to a plurality of pathogens can be evaluated simultaneously by analyzing the fluorescent signal associated with the different microparticles that have distinct spectral properties. The unique spectral addresses of the microparticle sets allow the different microparticle sets to be distinguished from each other.

The fluorescence emitted by the microparticle complexes coupled to specific fluorescent molecules can be detected by a flow cytometer or other detection instrument that is capable of both distinguishing between the unique characteristics defining a plurality of microparticle sets and detecting the fluorescence of the fluorescent label. Where one of skill in the art chooses to use microparticle sets that are distinguished by a unique spectral property, the detection instrument should comprise a method of distinguishing the spectral properties. For example, microparticle sets that are distinguished based on unique spectral properties can consist of distinguishing proportions of two or more fluorescent dyes. In such a case, the detection instrument should comprise a means for exciting the fluorescent dyes within the microspheres. Means for exciting fluorescent dyes include, but are not limited to, argon and krypton ion lasers, helium-neon lasers, helium cadmium lasers, diode lasers and solid-state lasers such as neodynium-YAG lasers.

An exemplary detection instrument of the present invention is a flow cytometer. Flow cytometry is a laser-based technology that is used to measure characteristics of biological particles. The underlying principle of flow cytometry is that light is scattered and fluorescence is emitted as light from the excitation source strikes the moving particles. This technology, when used in conjunction with the methods of the present disclosure, allows microparticle sets to be distinguished based on spectral properties of the labeled microparticle complexes. Additionally, it allows the presence of pathogen-specific antibodies specific to a plurality of pathogens of interest within a biological sample to de detected.

Automated flow cytometers for distinguishing microparticle sets and for measuring fluorescence emitted by fluorescent molecules are known in the art and can be adapted for use with the disclosed assays. Flow cytometers for use in the methods of the present disclosure are available commercially from several companies including Luminex Corporation (Austin, Tex.), Becton Dickinson (San Jose, Calif.), Beckman Coulter (Fullerton, Calif.) and Partec GmbH (Münster, Germany).

The following examples are provided to illustrate certain particular features and/or embodiments. These examples should not be construed to limit the disclosure to the particular features or embodiments described.

EXAMPLES

Example 1

Biotin Microsphere Immunoassay (MIA) to Detect Flavivirus Antibodies

This example describes the use of a biotin microsphere immunoassay (MIA) to detect West Nile (WN) virus and St. Louis Encephalitis (SLE) virus antibodies in serum samples. Although WN and SLE virus-specific antibodies are detected in this example, the biotin-MIA can be adapted to detect antibodies specific for any antigen of interest in serum samples from any animal species, including mammalian, avian and reptilian species.

Addition of Flavivirus Group-Reactive Antibody to Microspheres

Carboxylated microspheres pre-coupled to SLE monoclonal antibody 6B6C-1 were purchased from Radix Biosolutions (Georgetown, Tex.). The 6B6C-1 antibody recognizes E protein from both WN and SLE viruses. Purified flavivirus group-reactive SLE monoclonal antibody 6B6C-1 (Roehrig et al., *Virology* 128:118-126, 1983; Blitvich et al., *J. Clin. Microbiol.* 41(3):1041-1047, 2003) was covalently coupled by Radix Biosolutions to bead set numbers 32 and 57 (the coupled beads are referred to herein as "32-6B6C-1" and "57-6B6C-1") using the lot B method provided by Luminex Corporation. Briefly, 5 million beads were activated using 10 µl of 50 mg/ml sulfo-normal human serum (Pierce Chemical Co., Rockford, Ill.) and 10 µl of 50 mg/ml 1-ethyl-3(3-dimethylamino-propyl)carbodiimide-HCl at pH 6.3 in the dark for 20 minutes on a rotary mixer. Twenty-five µg of 6B6C-1 was coupled to the bead set at pH 6.0 with 2 hour incubation in the dark on the rotary mixer. Unused sites on the coupled microspheres were blocked with 1% bovine serum albumin in PBN (phosphate-buffered saline with 0.05% bovine serum albumin and 0.02% sodium azide) for 30 minutes. Bead concentration was adjusted to $2 \times 10^6$ beads/ml and stored in PBN at 4° C. (Johnson et al., *Clin. Diag. Lab. Immunol.* 12:566-574, 2005).

Flavivirus Antigens

Recombinant WN virus antigen (E-prM protein) expressed in COS-1 cells (Hennessy Research) and negative COS-1 antigen control (untransformed COS-1 cells processed in the same manner as the transformed cells) were purified by ultracentrifugation according to standard procedures. SLE negative antigen was obtained from the Centers for Disease Control's Division of Vector-Borne Infectious Diseases, Arboviral Diseases Branch (DVBID/ADB), Diagnostics and Reference Laboratory reference collection. SLE cross-reactivity-reduced antigen (often referred to as DRR antigen; Trainor et al. *Virology* 360(2): 398-406, 2007) was also obtained from the CDC.

Addition of Antigen to Antibody-Coupled Microspheres

To add antigen to antibody-coupled beads (32-6B6C-1 beads), 50 µl of well-vortexed beads was combined with 410 µl MIA buffer (PBS with 1% BSA, Sigma Chemical Company, St. Louis, Mo.) and either 40 µl WN antigen or 40 µl WN-negative antigen. Similarly, 57-6B6C-1 beads were added to 445 µl MIA buffer and either 5 µl SLE antigen or 5 µl SLE-negative antigen (when suckling mouse brain antigen is used). If SLE-DRR is used, the vortexed beads are combined with 410 µl MIA buffer and 40 µl SLE antigen or 40 µl SLE-negative antigen. Each sample was vortexed briefly and rotated for 1 hour on a tube rotisserie. Samples were stored at 4° C. until use (for up to one month).

Biotinylation of Serum Samples

Serum samples obtained from a variety of animal species were biotinylated according to the following procedure. Approximately 1 mg of biotin was used for every 30 samples being processed. 180 µl sterile water was added per 1 mg biotin. To each well of an ACROPREP™ filter plate, 44.5 µl of PBS and 4.25 µl biotin solution was added. For negative control and test serum samples, 1.25 µl of serum sample was added to the wells. For positive controls, 7.5 µl 6B6C-1 (37.5 µg) was added.

Samples were covered with plate sealer, vortexed briefly and placed on a plate shaker for 30 minutes. After 30 minutes, the plate sealer was removed from sample wells and maximum vacuum was applied on a vacuum manifold. When all wells were empty (the biotinylated antibodies are retained in the well even if the well appears dry), 50 µl of PBS was added to each well.

Microsphere Assay

Each serum sample was tested with virus antigen and negative antigen. An appropriate number of wells of a Millipore Multiwell plate were pre-wet with 100 nl of MIA buffer. To prepare the beads, 300 µl of each type of bead (WN antigen, WN-negative antigen, SLE antigen, SLE-negative antigen) and 2700 nl of MIA buffer were added to individual tubes. Next, 180 µl of MIA buffer was added to the appropriate number of wells on a low binding plate. Using a multichannel pipettor, 20 µl of each serum sample (after mixing) was added to the 180 µl of MIA buffer. Vacuum was reduced and the buffer was suctioned through the wells of the filter plate, without completing drying the wells.

The filter plate was placed on a flat surface. The antigen/bead complexes were vortexed thoroughly. To the viral antigen wells, 50 µl each of the WN and SLE antigen/beads were added. To the negative antigen well, 50 µl of both types of negative antigen/beads were added. Wells were washed twice on a vacuum manifold using 100 µl MIA buffer each time, taking care not to dry the beads.

Fifty µl of the diluted samples/controls was added to the wells, the plate was covered with a plate sealer and vortexed briefly. The underside was blotted with a paper towel. The sealed plate was covered with an aluminum foil-lined lid and placed on a shaker for 45 minutes. After 45 minutes, the samples were vacuumed through the wells and washed twice with 100 µl MIA buffer.

To prepare the conjugate, 48 µl streptavidin-phycoerythrin (PE) was added to 5952 µl MIA buffer. Fifty 50 µl of the diluted conjugate was added to each well. The wells were covered, vortexed briefly, blotted and shaken for 15 minutes. After the 15 minute incubation, wells were washed twice using 100 µl MIA buffer per well. MIA buffer (100 µl) was added back to each well. The underside of the wells were blotted, vortexed briefly and blotted again. Reactions were measured and analyzed using the BioPlex™ instrument (Bio-Rad Laboratories, Hercules, Calif.).

Results

Serum samples collected from multiple wild and domestic species, including wild-caught birds, mammals, reptiles and humans, were assayed for antibodies to WN virus and SLE virus. Specifically, the following species were tested: human, black bear, horse, cat, dog, squirrel, alligator, American kestrel, great horned owl, common barn owl, red tailed hawk, Swainson's hawk, eastern screech owl, golden eagle, red-winged blackbird, chicken, house sparrow, cliff swallow, American crow, great egret, rock pigeon, grackle, European starling, great blue heron, pheasant, ferruginous hawk, long-eared owl, prairie falcon, bald eagle, rough-legged hawk, burrowing owl and turkey vulture. Results were compared to those obtained using confirmatory tests. The infecting virus was reliably identified in most species using this method. Sample results are shown below in Table 1.

TABLE 1

Sample results obtained using biotin-MIA

| Species | Sample Type | WN (MFI) | SLE (MFI) |
|---|---|---|---|
| Bear | WN antibody-positive confirmed | 14819 | 2376 |
| Bear | Confirmed negative | 186 | 424 |
| Alligator | WN antibody-positive confirmed | 3381 | 970 |
| Alligator | Confirmed negative | 71 | 97 |
| Chicken | SLE antibody-positive confirmed | 1334 | 6680 |
| Chicken | Confirmed negative | 760 | 599 |
| Golden eagle | WN antibody-positive confirmed | 10693 | 1390 |
| Golden eagle | Confirmed negative | 408 | 106 |

MFI = Median fluorescence intensity

Figure 2:
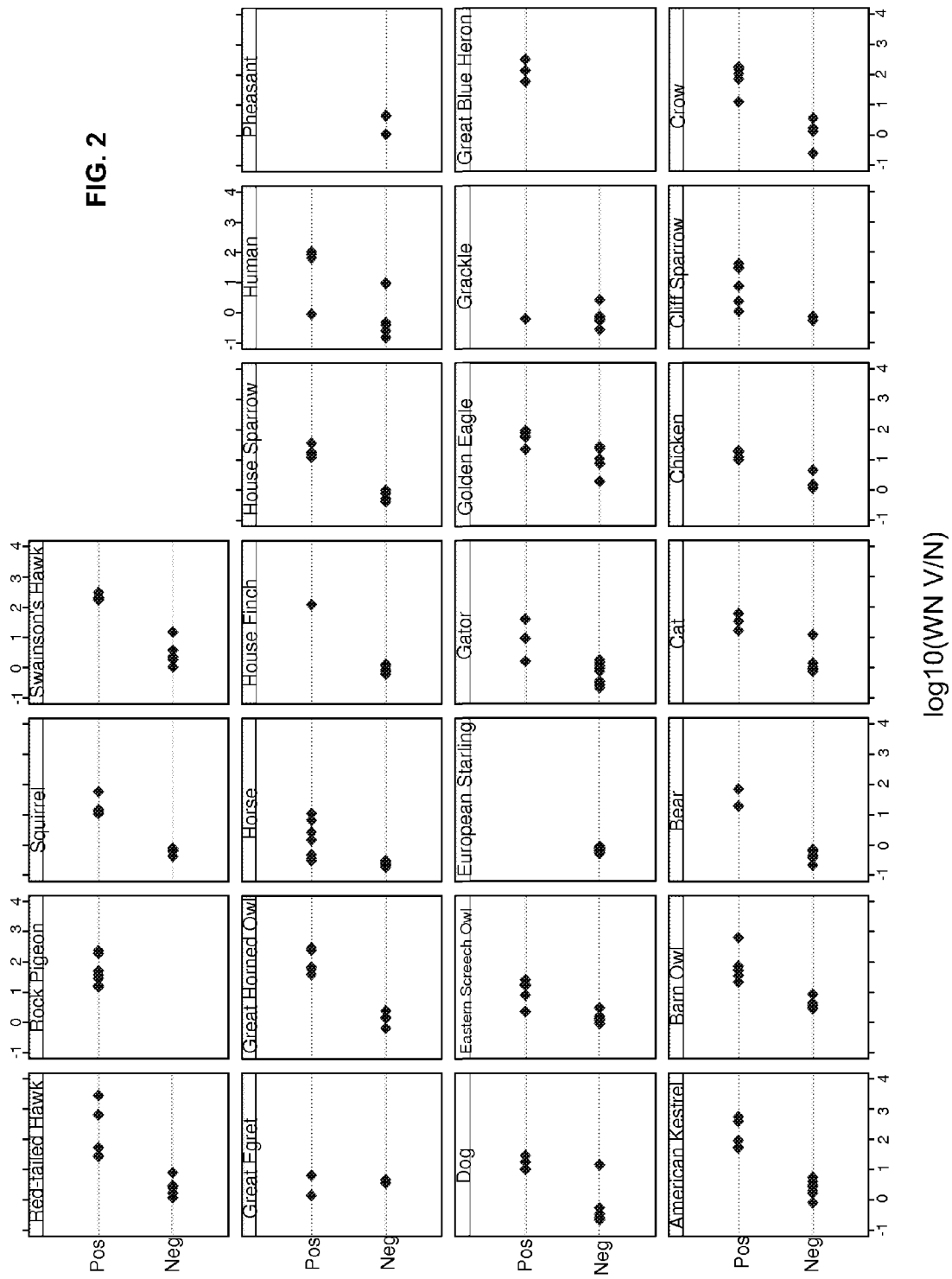
FIG. 2 is a series of graphs showing the ratio of West Nile virus antigen reaction to negative antigen reaction for a variety of mammalian, reptilian and avian species tested using a biotin microsphere-based immunoassay (MIA). Each diamond represents an individual sample. On the Y-axis, "Pos" indicates samples that tested positive for West Nile viral antigen by plaque-reduction neutralization test (PRNT) and "Neg" indicates samples that tested negative for West Nile viral antigen by PRNT. The X-axis shows $\log_{10}$ West Nile viral antigen reaction versus negative antigen reaction for each sample. For the majority of species, biotin-MIA was able to distinguish samples that tested positive for West Nile viral antigen by PRNT from those that tested negative by PRNT.

FIG. 2 shows results of the biotin-MIA using samples from a variety of mammalian, reptilian and avian species. Each sample (represented by the diamonds) was designated as either "Pos" or "Neg" depending on whether the sample tested positive or negative, respectively, for West Nile viral antigen by PRNT. The results are shown as $\log_{10}$ West Nile viral antigen reaction versus negative antigen reaction for each sample. For the majority of species, the biotin-MIA assay was able to distinguish samples that tested positive for West Nile viral antigen by PRNT from those that tested negative by PRNT.

Figure 3:
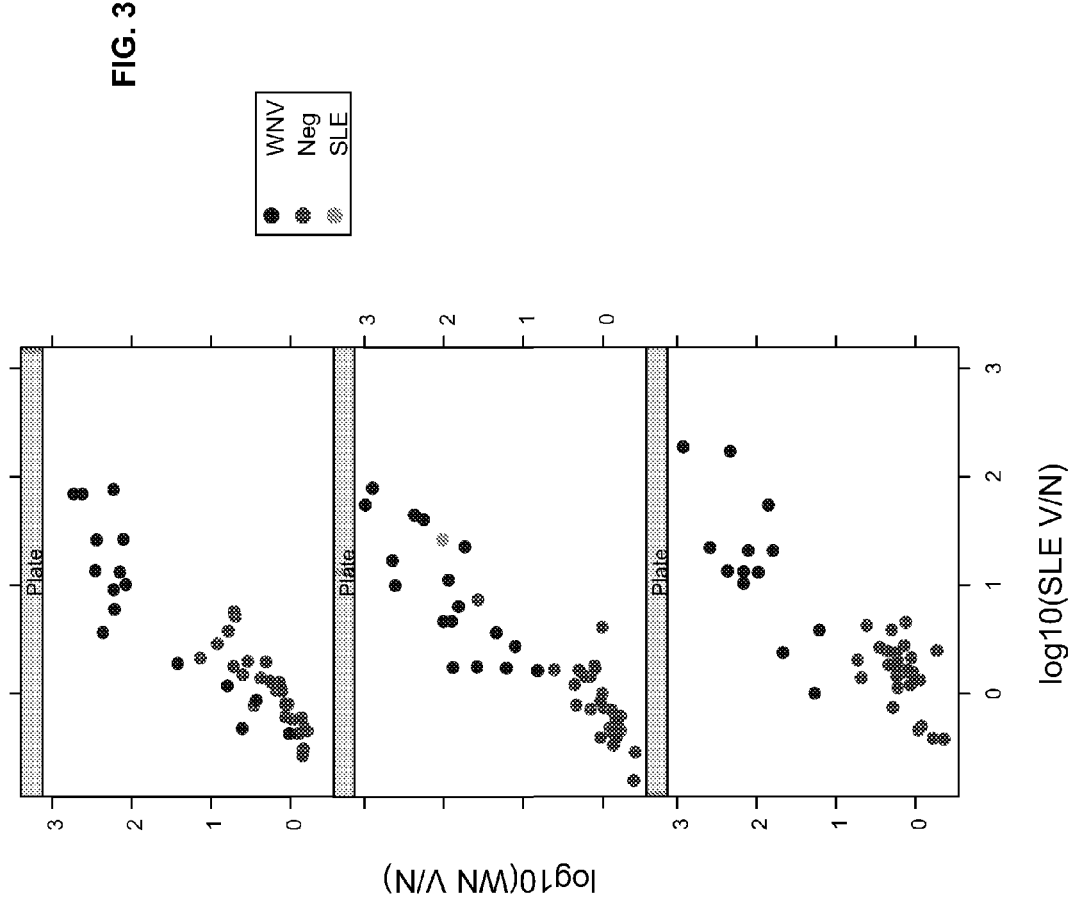
FIG. 3 is a series of graphs showing the results of biotin-MIA in bird samples for three separate experiments. Dots represent samples that tested positive for West Nile (WN) virus antigen, positive for St. Louis encephalitis (SLE) virus antigen, or negative for both by PRNT. Pooled sera from several avian species was used as the negative control. The results are plotted as $\log_{10}$ WN viral antigen reaction versus negative antigen reaction on the Y-axis and $\log_{10}$ SLE viral antigen reaction versus negative antigen reaction on the X-axis.

For some species, such as wild avian species, an appropriate negative control is not always available. To test whether a pooled negative control could be effectively used in the biotin-MIA assay, a pooled negative control was made from the serum of five different avian species: *Galliforme* (domestic chicken), *Ciconiiforme* (great egret), *Falconiforme* (Swainson's hawk), *Strigiforme* (eastern screech owl) and *Passeriforme* (house finch). 6B6C-1 was used as the positive control. The results of three separate experiments (plates) are shown in FIG. 3. Dots represent samples that tested positive for West Nile (WN) virus antigen, positive for St. Louis encephalitis (SLE) virus antigen, or negative for both by PRNT. The results are plotted as $\log_{10}$ WN viral antigen reaction versus negative antigen reaction on the Y-axis and $\log_{10}$ SLE viral antigen reaction versus negative antigen reaction on the X-axis. Using the biotin-MIA assay, most confirmed-negative samples were distinguishable from confirmed-positive samples. In addition, very little plate to plate variation is observed, indicating that the pooled negative control can be effectively used in this assay.

Figure 4:
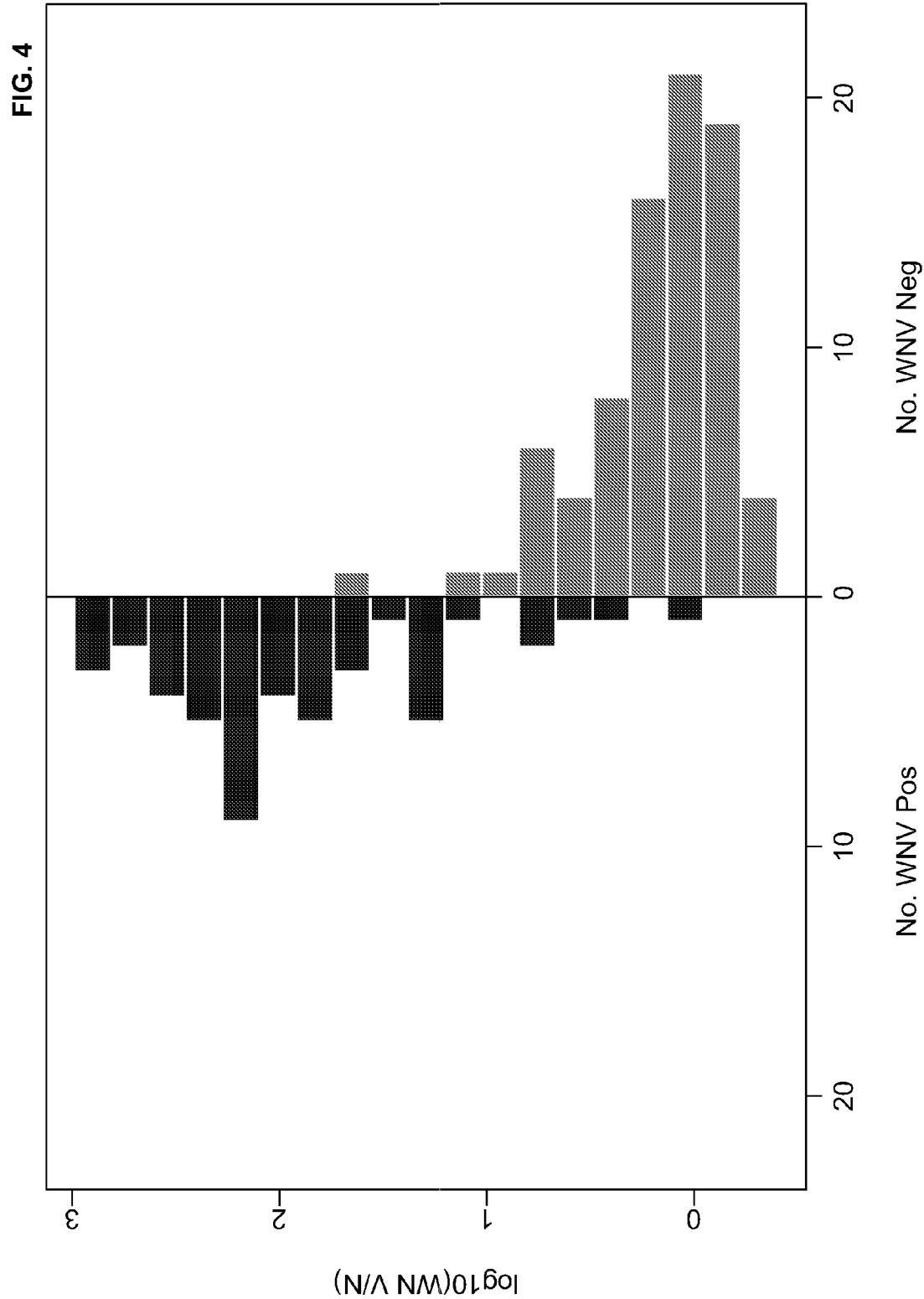
FIG. 4 is a bar graph showing the distribution of WN positive and negative samples. Shown are the number of PRNT confirmed-positive WN samples and confirmed-negative samples for each $\log_{10}$ value obtained using biotin-MIA. Little overlap is observed between positive and negative samples.
Figure 5:
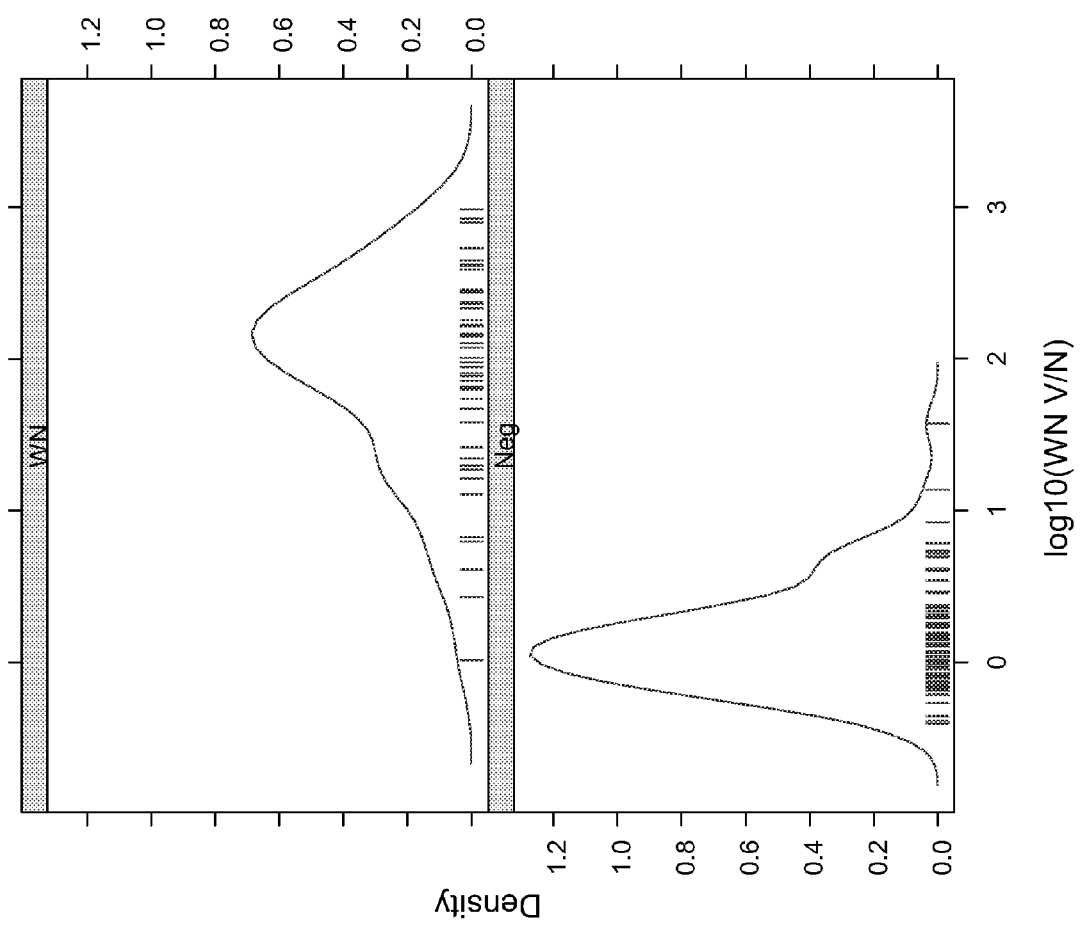
FIG. 5 is a line graph showing the distribution of WN positive and negative samples. Shown is the distribution of PRNT-confirmed positive WN samples (top) and confirmed-negative samples (bottom) relative to the $\log_{10}$ value obtained using biotin-MIA. Short vertical bars indicate individual samples.

FIG. 4 illustrates the distribution of WN positive and WN negative samples. Shown are the number of PRNT confirmed-positive WN samples and confirmed-negative WN samples for each $\log_{10}$ value obtained using biotin-MIA. Little overlap is observed between positive and negative samples. FIG. 5 is a graphical representation of the same data. WN positive samples are shown in the top graph and negative samples are shown in the bottom graph. Short vertical bars indicate a sample. As shown in the figure, the positive and negative groups have very little overlap.

Figure 6:
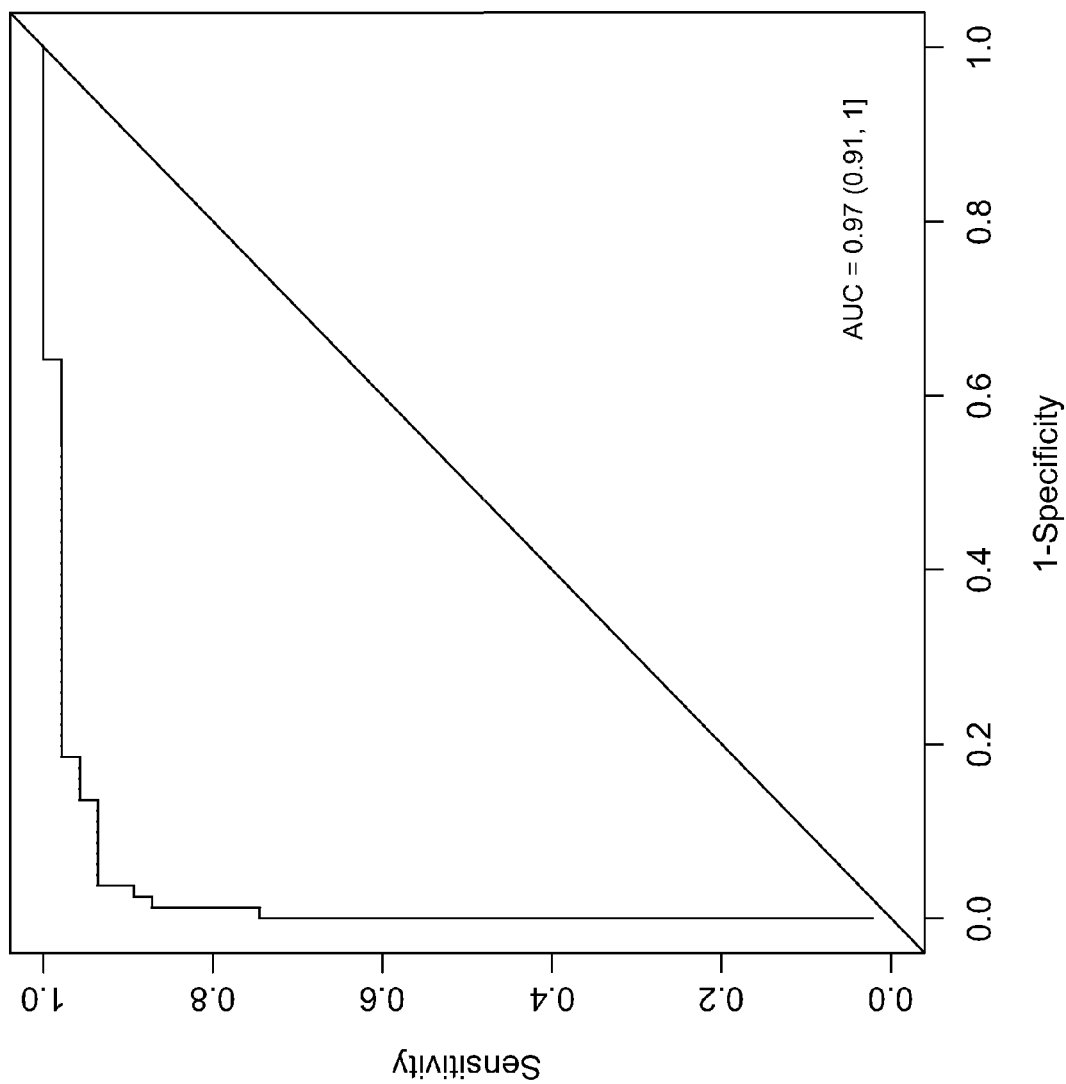
FIG. 6 is a graph showing the results of receiver operator characteristics (ROC) analysis of biotin-MIA using WN and negative samples from various species. Sensitivity (y-axis) is plotted against specificity (x-axis). Area under the curve (AUC) was calculated to be 97%.
Figure 7:
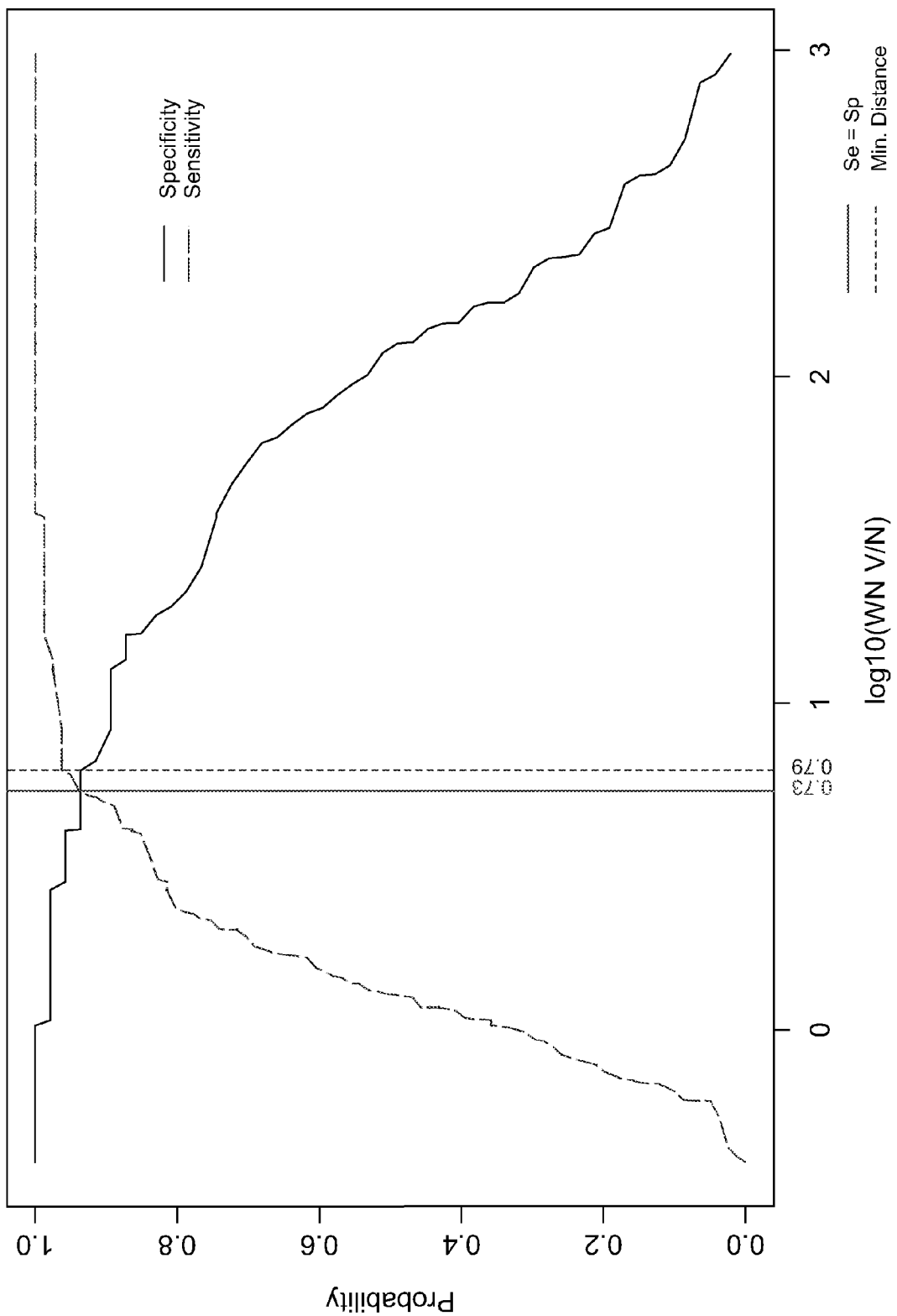
FIG. 7 is a graph illustrating sensitivity (dashed line) and specificity (solid line) of biotin-MIA. Probability is plotted against $\log_{10}$ WN viral antigen reaction versus negative antigen reaction for each sample. The vertical line indicates where sensitivity equals specificity (0.73). The dashed line indicates the minimum distance (0.79), the point where both the sensitivity and sensitivity are maximized to optimize results.

FIG. 6 shows the results of receiver operator characteristics (ROC) analysis of the assay using samples from various species. Sensitivity (y-axis) is plotted against specificity (x-axis). Area under the curve (AUC) was calculated to be 97%, indicating that biotin-MIA is a very good diagnostic assay. FIG. 7 is a graph plotting sensitivity (dashed line) and specificity (solid line). The vertical line indicates where the two lines cross (sensitivity=specificity; 0.73). The dashed line represents the point where both the sensitivity and sensitivity are maximized to optimize results (0.79). These results are also provided in Table 2.

TABLE 2

Sensitivity and specificity of biotin-MIA

| Test | | WNV PRNT | | Performance | |
| --- | --- | --- | --- | --- | --- |
| | | Pos | Neg | Sensitivity | Specificity |
| log10 (V/N) ≥ 0.73 | Pos | 106 | 15 | 0.88 (0.81, 0.93) | 0.92 (0.87, 0.95) |
| | Neg | 14 | 163 | | |
| log10 (V/N) ≥ 0.79 | Pos | 106 | 14 | 0.88 (0.81, 0.93) | 0.92 (0.87, 0.95) |
| | Neg | 14 | 164 | | |
| Total | | 120 | 178 | | |

Figure 8:
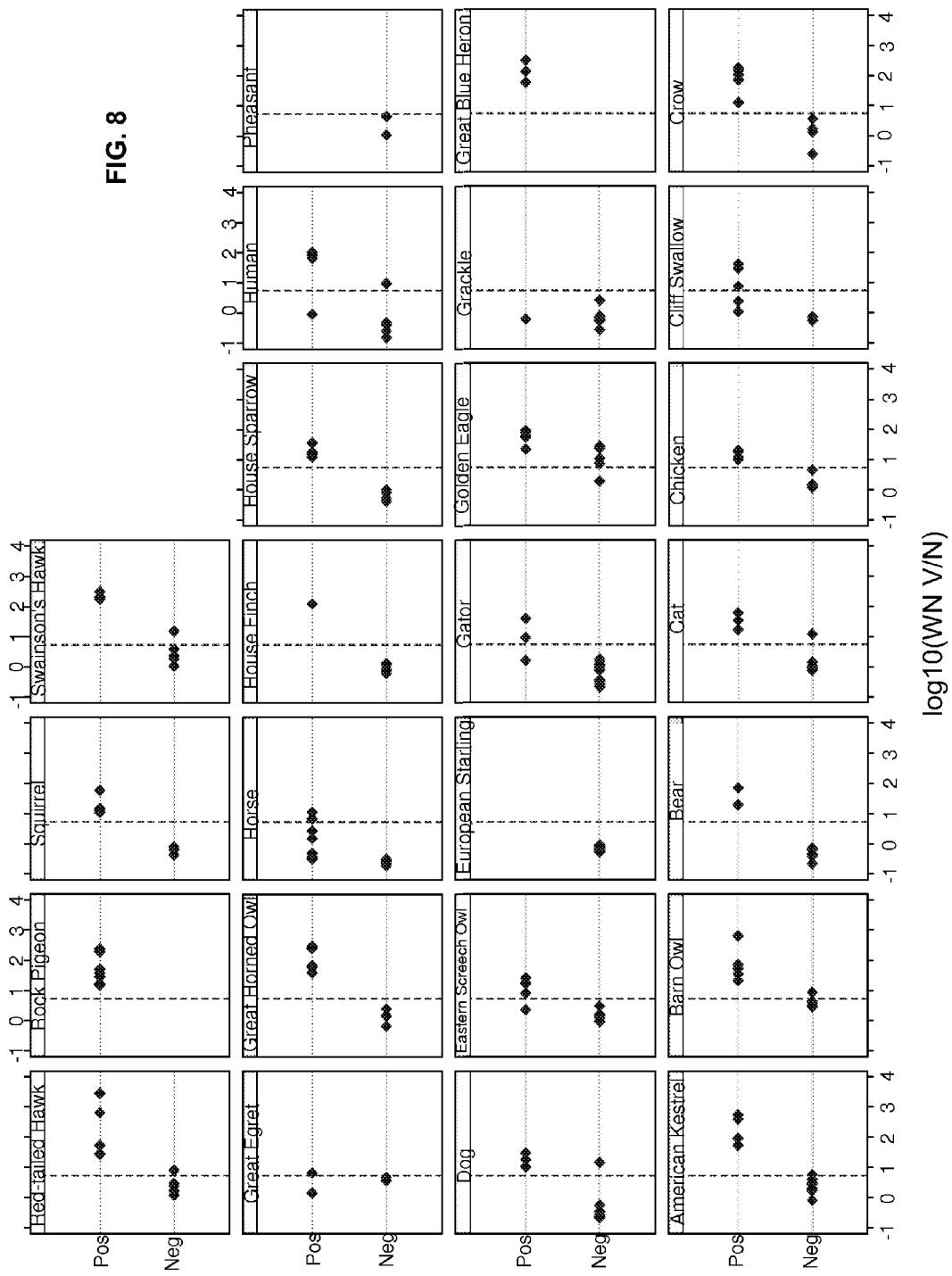
FIG. 8 is a series of graphs showing the ratio of WN virus antigen reaction to negative antigen reaction for a variety of mammalian, reptilian and avian species tested using biotin-MIA. The data points are shown relative to the value where sensitivity equals specificity (0.73), which is indicated by the dashed line.

To further evaluate for which species biotin-MIA is an effective diagnostic assay, the sensitivity/specificity data was applied to previous results obtained in mammalian, reptilian and avian species. FIG. 8 shows the same data as in FIG. 2, however the data points are shown relative to the point where sensitivity equals specificity (0.73), indicated by the dashed line. If the assay works well for a particular species, then the negative data points should be to the left of the dashed line, while the positive data points should be to the right of the dashed line. For example, biotin-MIA effectively separates positive and negative samples for red-tailed hawk, great horned owl, bear and other species.

Figure 9:
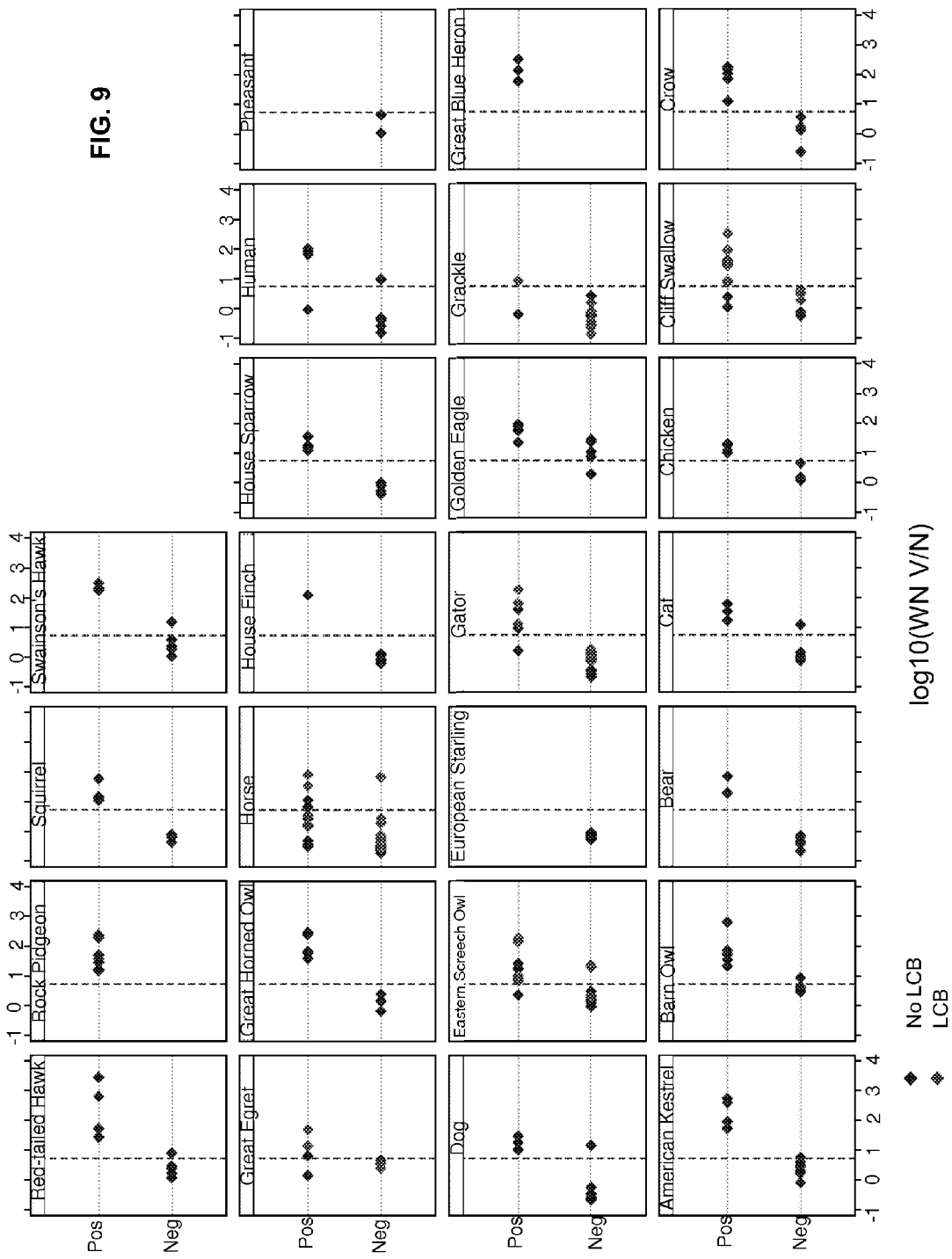
FIG. 9 is a series of graphs showing the ratio of WN virus antigen reaction to negative antigen reaction for a variety of mammalian, reptilian and avian species tested using biotin-MIA. This data is identical to the data shown in FIG. 8, except that samples for the great egret, horse, eastern screech owl, alligator, grackle and cliff swallow species were retested using low cross buffer (LCB) as a serum diluent. Black diamonds indicate the original data and grey diamonds indicate samples processed using LCB. Many of the false negatives were eliminated using LCB.

For several species, false negatives occurred due to a high amount of background. To minimize false negatives, low cross buffer (LCB) (Candor Bioscience GmbH, Germany) was used as a serum diluent for great egret, horse, eastern screech owl, alligator, grackle and cliff swallow. FIG. 9 shows the results of this data compared to the original data. Many of the false negatives were eliminated using LCB.

Taken together, these results indicate the biotin-MIA is an effective diagnostic assay having high specificity and sensitivity in a wide variety of wild and domestic animal species.

Example 2

Biotin-MIA to Detect WN, SLE and EEE Antibodies

This example summarizes the results of the analysis of 497 serum samples obtained from a variety of avian, mammalian and reptilian species. Samples were obtained from the following species: *Aquila chrysaetos* (golden eagle); *Ardea alba* (great egret); *Ardea herodias* (great blue heron); *Bubo virginianus* (great horned owl); *Buteo jamaicensis* (red-tailed hawk); *Buteo swainsoni* (Swainson's hawk); *Carpodacus mexicanus* (house finch); *Columba livia* (rock pigeon); *Corvus brachyrhynchos* (American crow); *Falco sparverius* (American kestrel); *Gallus domesticus* (chicken); *Megascops asio* (eastern screech owl); *Passer domesticus* (house sparrow); *Petrochelidon pyrrhonota* (cliff swallow); *Phasianus colchicus* (common pheasant); *Quiscalus quiscula* (common grackle); *Sturnus vulgaris* (European starling); *Tyto alba* (barn owl); *Canis lupis familiaris* (dog); *Equus caballus* (horse); *Felis domesticus* (cat); *Homo sapiens* (human); *Sciurus niger* (fox squirrel); *Ursus americanus* (American black bear); and *Alligator mississippiensis* (American alligator).

Materials and Methods
Biotinylation of Serum Samples

For development of the tests, a total of 298 serum samples were biotinylated using a 50-molar excess of biotin over calculated amines as optimized by titration. To 1.25 µl of serum, 4.25 µl of 5.55 mg/ml sulfo-LC-biotin (Pierce, Rockford, Ill.) and 44.5 µl of PBS pH 7.4 were added. Samples were incubated for 30 minutes with mixing at room temperature in wells of a 100 KDa molecular weight cut-off filter plate (Acroprep 100, VWR Scientific, San Francisco, Calif.) using a Lab-Line instruments rotary titer plate shaker at 900 rpm (VWR). Components with molecular weights <100 KDa, primarily albumin and uncoupled biotin, were removed via vacuum filtration. The retentate, enriched for biotinylated antibodies, was washed with 50 µl PBS, then vacuum-filtered and resuspended in 50 µl PBS, which constituted a 1:40 dilution of the original sample. Candor Low Cross Buffer (LCB) (Boca Scientific, Boca Raton, Fla.) was used to make further 1:10 dilutions of the samples for final serum dilutions of 1:400, which was determined by initial titration to yield optimal signal-to-noise ratios.

Controls

The following purified monoclonal antibodies (MAbs) served as positive controls and were treated using the same method as for the serum samples: 25 µg flavivirus group-reactive MAb 6B6C-1 (Roehrig et al., *Virology* 128:118-126, 1983) for the WN/SLE biotin-MIA and 25 µg alphavirus group-reactive MAb 1A4B-6 for the EEE biotin-MIA (Roehrig et al., *Am. J. Trop. Med. Hyg.* 42:394-398, 1990). Known antibody-negative sera from representatives of each order of birds, mammals and reptiles represented in the test sample set were pooled. This was used as a negative control where 1.25 µl of the pool was biotinylated in the same way as the samples.

Biotin-MIA

Two biotin-MIA methods were developed, the WN/SLE biotin-MIA and the EEE biotin-MIA. MicroPlex microsphere sets 32 and 57 (Luminex Corp., Austin, Tex.) coupled covalently using standard carbodiimide chemistry (Staros et al., *Anal. Biochem.* 156:220-222, 1986) with MAb 6B6C-1 for the WN and SLE viral antibody tests respectively, were purchased from Radix Biosolutions (Georgetown, Tex.). Set 15 coupled to alphavirus group-reactive MAb 2A2C-3 (Hunt and Roehrig, *Virology* 142:334-346, 1985) for the EEE viral antibody test was also purchased from Radix Biosolutions. Prior to performing the assay, microspheres were reacted with each viral antigen and its corresponding negative control antigen in PBS/1% BSA (Sigma-Aldrich, St. Louis, Mo.) by mixing at room temperature for 1 hour. These reactions were performed for each antigen at a rate of 5000 microspheres per microliter as follows: 50 µl set 32-6B6C-1 plus either 40 µl WN virus recombinant antigen (Hennessy Research, Kansas City, Mo.) (Davis et al., *J. Virol.* 75:4040-4047, 2001) or 40 µl negative recombinant antigen (Hennessy Research) plus 410 µl PBS/1% BSA; 50 µl set 57-6B6C-1 plus either 40 µl SLE virus recombinant antigen (Trainor et al., *Virology* 360:398-406, 2007) or 40 µl negative recombinant antigen plus 410 µl PBS/1% BSA; 50 µl set 15-2A2C-3 plus either 2 µl EEE suckling mouse brain antigen or 2 µl negative suckling mouse brain antigen plus 448 µl PBS/1% BSA.

Preparations were stored at 4° C. and were used the following day or for up to a month thereafter. For each of 248 samples used to develop the WN/SLE biotin-MIA, 2500 viral antigen-reacted set 32 and 57 microspheres suspended in a total volume of 100 µl PBS/1% BSA (Sigma-Aldrich, St. Louis, Mo.) were added to a single well of a 96-well filter plate (Millipore Corp., Billerica, Mass.). Negative antigen-reacted sets 32 and 57 were added to a different well. The microspheres were washed twice with 100 µl PBS/1% BSA on a vacuum manifold. Fifty microliters of prepared sample or controls were added to the wells containing viral or negative antigen-coupled microspheres, which were shaken for 45 minutes at room temperature on a titer plate shaker at 900 rpm. Wells were washed twice with 100 µl PBS/1% BSA, followed by the addition of 50 µl per well of 4 µg/ml streptavidin-phycoerythrin (Jackson Immunoresearch, West Grove, Pa.) in PBS/1% BSA. Plates were shaken for 15 minutes then washed twice. Microspheres were resuspended in 100 μl per well of PBS/1% BSA.

Reactions were read using a BioPlex instrument (Bio-Rad Laboratories, Hercules, Calif.), where microsphere sets and the biological reactions associated with them were identified and quantified via a combination of lasers. Raw results were expressed as median fluorescent intensities (MFIs) of 100 microspheres per sample per set. An identical scheme was used for the EEE assay with 50 samples reacted on viral and negative antigen-coupled set 15 microspheres.

Plaque Reduction Neutralization Tests

All biotin-MIA results were compared to those of the plaque reduction neutralization test (PRNT) (Beaty et al., 1995, Arboviruses, p. 189-212, In L. D. Lennette E H and Lennette E T (ed.), Diagnostic procedures for viral, rickettsial and chlamydial infections, 7$^{th}$ ed. American Public Health Association, Washington, D.C.), the gold standard serologic method in arbovirology, using 90% plaque reduction to indicate a positive result at a minimum serum dilution of 1:10.

Determination of Cut-Offs

For each of the antigens, test success and cut-off values that classified samples as being antibody-positive or negative to each virus were determined by comparing the results obtained in the biotin-MIAs to those of PRNT using Receiver Operator Characteristic (ROC) curves (M. S. Pepe, The Statistical Evaluation of Medical Tests for Classification and Prediction, Oxford University Press, New York, 2003). Areas under the ROC curves (AUC) and associated 95% confidence intervals (CI) were calculated (Newcome, Stat. Med. 25:559-573, 2006). Results that were used in the determination of the ROC curves for the WN/SLE biotin-MIA pertained only to the infecting virus as determined via PRNT, to avoid skewing the results by the inclusion of apparent false positives caused by sera reactive to both flavivirus antigens. Similarly, false-positive and false-negative rates took this into account. Leave-one-out cross-validation was used to estimate predictive performance of the cut-off determination procedure.

Cross-Reactivity Assays

Cross-reactivity of anti-arboviral antibodies to arboviral antigens is well-documented (Johnson et al., J. Clin. Microbiol. 38:1827-1831, 2000). For the WN/SLE biotin-MIA, cross-reactivity was estimated using 42 archived human diagnostic samples from confirmed infections of other flaviviruses, Japanese encephalitis (JE) virus and dengue (DEN) virus; alphaviruses EEE virus and Chikungunya (CHIK) virus; and bunyavirus La Crosse encephalitis (LAC) virus. For the EEE biotin-MIA, samples from 10 confirmed human CHIK virus infections, and 13 chicken WN virus infections were used to determine cross-reactivity with antibodies to these viruses.

Validation

Following development, the WN/SLE biotin-MIA was validated using 134 avian sera from the following species: *Tyto alba; Pica pica; Falco sparverius; Buteo regalis; Buteo jamaicensis; Megascops asio; B. swainsoni; Asio otus; F. mexicanus; Cathartes aura; Haliaeetus leucocephalus; B. lagopus; Athene cunicularia; Accipiter gentilis; Passer domesticus; Petrochelidon pyrrhonota; Bubo virginianus; Corvus brachyrhynchos; Sturnus vulgaris; Quiscalus quiscula; Columba livia; Carpodacus mexicanus; Phasianus colchicus; Agelaius phoeniceus; Ardea alba*; and *A. herodias*. All samples were known to be either WN antibody-positive or antibody-negative.

Results

For each sample, the MFI value obtained when reacted on each of the viral antigens (V) was divided by the MFI to the corresponding negative antigen reaction (N) to yield a V/N value, which was used in further computations. The negative serum control pool gave MFIs of less than 350 when reacted on the viral antigens, and positive controls were always greater than 1000 MFI when reacted on the viral antigens. Negative samples gave MFIs generally in the range of 50-350 and positive samples gave MFIs generally in the range of 1000-25,000, when reacted on viral antigens.

Figure 10:
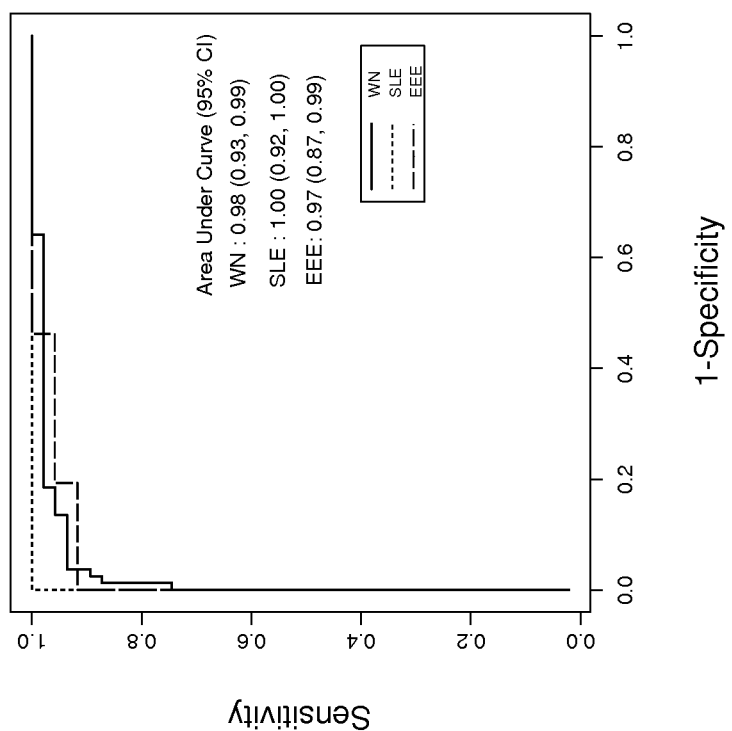
FIG. 10 is a graph showing receiver operator characteristic (ROC) curves for WN, SLE and eastern equine encephalitis (EEE) viral antigens in biotin-MIAs. Sensitivities and specificities for each antigen were calculated using the results from PRNT as the standard. Areas under the curve and 95% confidence intervals are shown.
Figure 11:
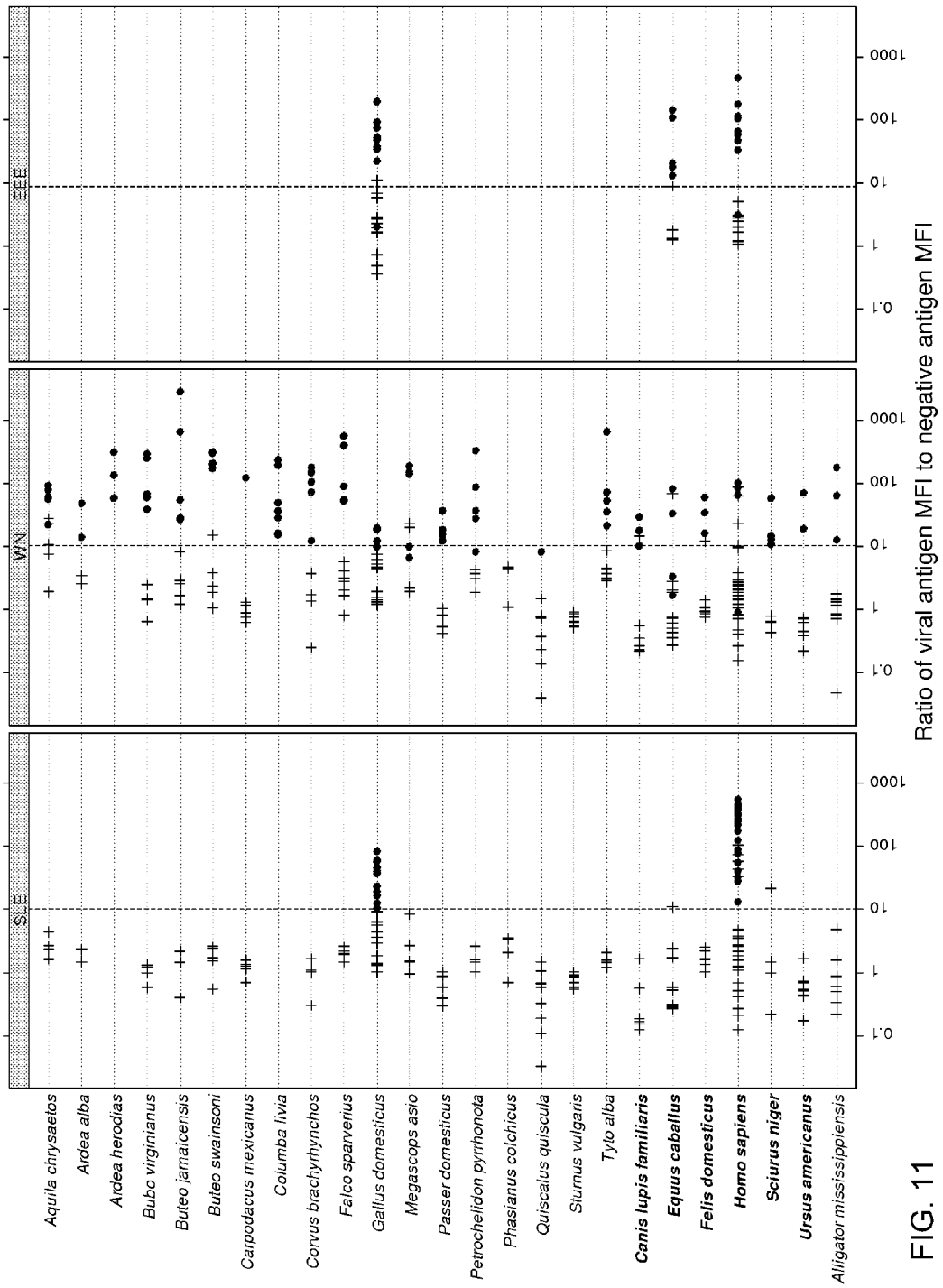
FIG. 11 is a graph showing viral antigen to negative antigen (V/N) ratios for 346 serum samples obtained from a variety of species. PRNT-negative samples are indicated by plus (+) signs and PRNT-positive samples are indicated by black dots. For WN/SLE biotin-MIA, results are shown for known negatives, and for positives to the homologous viral antigens only. The dashed vertical line on each panel represents the positive V/N cut-off for that antigen. Species are listed in the following order: birds (upper, normal type); mammals (bold type); and reptile (lower, normal type).

The ROC plots generated for each virus (FIG. 10) gave AUCs of greater than 90%, indicating good discrimination ability of the tests. Initial results indicated that a small number of species (*Alligator mississippiensis, Ardea alba, Equus caballus, Megascops asio, Petrochelidon pyrrhonota* and *Quiscalus quiscula*) were susceptible to background reactivity with the negative antigens in the WN/SLE biotin-MIA when PBS/1% BSA was used as the final 1:10 diluent. This problem was mitigated by the use of Candor LCB and did not alter results obtained from other species. Therefore this reagent was adopted as standard in the protocol. Approximately equal numbers of antibody-positive and negative samples were used in the development of these tests, where at least half in the WN/SLE biotin-MIA originated from wild-caught species (FIG. 11).

Sensitivity and specificity data for each virus as plotted in the ROC curves were used to derive V/N cut-off values above which samples are deemed positive for the respective viruses. Because all the sensitivity and specificity values were >90%, cut-offs were chosen such that sensitivity=specificity. Cut-off values were: WN 10.00; SLE 10.23; EEE 8.97. FIG. 11 shows the biotin-MIA results for all species tested for all viruses with respect to PRNT, with the calculated cut-offs applied for each virus. Respectively, false-positive and false-negative rates computed using these cut-offs were: WN 5.5%, 5.8%; SLE 0.0%, 0.0%; EEE 0.0%, 4.0%. The overall accuracy of the WN/SLE biotin-MIA was 94.4% and the overall accuracy of the EEE biotin-MIA was 98.0%. Cross-validation estimates of predictive error mirrored these empirical results, with prediction errors given as (overall, false-positive, false-negative): WN (5.5%, 6.4%, 4.9%); SLE (1.8%, 0.0%, 4.8%); EEE (6.0%, 8.3%, 3.8%). Repeatability was measured at 100% (95% CI 80.6-100.0%) for 16 samples tested on the same plate at the same time, and reproducibility was measured at 95.2% (95% CI 77.3-99.8%) for 21 samples measured on different days on different plates on different instruments. These last 2 parameters were for the WN/SLE biotin-MIA only, using a variety of samples that were known WN or SLE antibody-positive, or negative.

Cross-reactivity results are shown in FIG. 12. Both the WN and SLE viral antigens in the WN/SLE biotin-MIA (FIG. 12A) showed significant cross-reactivity against sera from human flavivirus infections of JE virus (1 sample out of 6) and DEN virus (4 samples out of 10). No cross-reactivity was observed with sera with antibodies to alphaviruses EEE virus (0/10) and CHIK virus (0/6), or against bunyavirus LAC virus (0/10). Human sera positive for anti-CHIK virus antibodies showed minimal cross-reactivity (1/10) and chicken anti-WN antibodies showed no cross-reactivity (0/13) with the EEE biotin-MIA (FIG. 12B).

Validation of the WN portion of the WN/SLE biotin-MIA was performed using samples that had been previously tested for antibodies to WN virus by PRNT but were not included in cut-off determination. Using the cut-off of V/N=10.00 for WN, the WN/SLE biotin-MIA gave a false positive rate of 0% (95% CI 95.6-100.0%; 84/84 negatives were correctly identified), and a false negative rate of 10% (95% CI 78.6-95.6%; 45/50 WN positives were correctly identified).

A previous study compared specimens from WN virus-infected humans in a WN IgM-ELISA and SLE IgM-ELISA (Martin et al., *Clin. Diagn. Lab. Immunol.* 11:1130-1133, 2004). It was consistently found that the optical densities (ODs) of the test specimens divided by the OD of the negative control serum when reacted on WN viral antigen, was at least three times greater than when reacted on SLE viral antigen. The reverse was not true of SLE-viral infections. Similar comparisons in the WN/SLE biotin-MIA showed that V/Ns for the WN viral antigens were consistently 2-fold or greater than those obtained with the SLE-viral antigen when WN was the infecting virus. In humans, if SLE was the infecting virus, a 2-fold difference in V/Ns was not observed, although the V/Ns were consistently higher for SLE infections for the limited number of samples tested. For chickens, however, SLE virus infections were distinguishable with minimum SLE-to-WN V/N ratio of 6:1.

Example 3

Detection of Antigen-Specific Engineered Antibodies in Plants

Plants can be engineered to express antibodies or antibody fragments to protect the plant from plant pathogens or to produce antibodies or diagnostic or therapeutic purposes. The method of detecting antigen-specific antibodies in a biological sample can be used to detect antigen-specific engineered antibodies in plants.

To detect antigen-specific antibodies in plants, a protein extract is prepared from the plant, or suitable portion of the plant, such as the leaves, according to standard procedures (see, for example, Di Carli et al., *J. Proteome Res.* 8:838-848, 2009; and Franconi et al., *Immunotechnology* 4:189-201, 1999). Several exemplary protein extraction procedures are provided below. However, it is understood that any method used to prepare a protein extract from plant material can be used in the method.

Protocol A: Phenol extraction is performed according to previously reported procedures (see Kurkman and Tanaka, *Plant Physiol.* 81:802-806, 1986). Leaf tissue (1 gram) is finely powdered in liquid $N_2$ and homogenized in 1 mL of 0.5 M Tris-HCl, pH 7.5, 1 M NaCl, 500 mM EDTA, 50 mM DTT, containing complete protease inhibitors (Roche). An equal volume of phenol saturated solution in 0.5 M Tris-HCl, pH 8.0, is then added. This mixture is subjected to vortexing for 1 minutes, followed by cooling on ice. After centrifugation at 3500×g for 10 minutes, the aqueous phase is removed without disrupting the liquid interface containing most of the proteins. This step is repeated, adding 2 volumes of phenol saturated solution in 0.5 M Tris-HCl, pH 8.0. Proteins are precipitated with 5 volumes of 0.1 M ammonium acetate in cold MeOH, at −20° C., overnight. Supernatant is removed after centrifugation at 3500×g for 10 minutes at 4° C. The pellet is suspended in 0.1 M ammonium acetate and 80% (v/v) cold MeOH. The protein pellet obtained after a new centrifugation at 3500×g for 10 minutes at 4° C. is rinsed with 80% (v/v) acetone and again subjected to centrifugation at 3500×g for 10 minutes at 4° C. The final pellet is dried to remove traces of acetone.

Protocol B: Phenol extraction is carried out in the presence of SDS according to Wang et al. (*Electrophoresis* 24:2369-2375, 2003). Leaf tissue powder is dissolved in 8 volumes of phenol saturated solution in 0.5 M Tris-HCl, pH 8.0, and 8 volumes of SDS buffer (30% sucrose, 2% SDS, 0.1 M Tris-HCl, pH 8.0, 5% DTT). After vortexing, the upper phenol phase is collected by centrifugation at 8000×g for 5 minutes; this step was repeated twice. Proteins are precipitated adding 5 volumes of 0.1 M ammonium acetate in cold MeOH at −20° C. for 30 minutes. The pellet is recovered by centrifugation at 8000×g for 10 minutes, and then rinsed 3 times with 0.1 M ammonium acetate in cold MeOH and 3 times with 80% cold acetone. The final pellet is dried.

Protocol C: Protein extraction by aqueous buffer associated to TCA-acetone precipitation is performed according to Saravanan and Rose (*Proteomics* 4:2522-2532, 2004), with minor modifications. Powdered leaves (5 grams) are suspended in a 1% PVPP, 0.1 M KCl, 0.5 M Tris-HCl, pH 7.5, 500 mM EDTA, 2% DTT buffer, containing complete protease inhibitor cocktail (Roche) (15 mL). The mixture is homogenized using an Ultraturrax homogenizer for 15 minutes at 4° C. The insoluble material is removed by centrifugation at 6000×g for 60 minutes at 4° C. Proteins present in the supernatant are precipitated with 20 mL of cold acetone containing 10% TCA, 1% PVPP and 2% DTT, at −20° C. overnight. The protein pellet is recovered by centrifugation at 6000×g for 60 minutes at 4° C., rinsed once with cold MeOH, 3 times with cold acetone, and finally dried.

Protocol D: TCA-acetone extraction is adapted from the method of Tsugita et al. (*Methods Mol. Biol.* 112:95-97, 1999) with some modifications. Leaf tissue (2 grams) is ground to a fine powder in a mortar with liquid $N_2$. The resulting powder is finely homogenized in cold acetone using an Ultraturrax homogenizer and recovered by centrifugation at 8000×g for 30 minutes at 4° C. The pellet is suspended in 8 mL of 10% TCA and 2% DTT, containing complete protease inhibitor cocktail (Roche) in cold acetone. Proteins are precipitated at −20° C. overnight, and then are collected by centrifugation at 8000×g for 1 hour. The protein pellet is then mixed with 0.07% DTT containing protease inhibitor cocktail in cold acetone and placed at −20° C. for 1 hour. The pellet is collected by centrifugation at 8000×g for 1 hour at 4° C., washed at least 3 times with cold acetone until the supernatant is colorless, aliquotted, and lyophilized.

Protocol E: A variation of Protocol D in which the DTT is replaced by 0.07% β-mercaptoethanol in all steps.

Protocol F: A variation of Protocol D in which the concentration of DTT in the TCA-acetone extraction buffer is reduced to 0.07%. Moreover, an additional precipitation step is performed. After TCA/acetone precipitation, the pellet is suspended in 5 M urea, 2 M thiourea, 30 mM Tris-HCl, pH 8.0, 2% CHAPS, 1% Triton X-100 and 50-60% ammonium sulfate is added to obtain a saturated solution. Proteins are precipitated overnight at 4° C., and collected by centrifuging at 8000×g for 1 hour at 4° C.

Protocol G: A variation of Protocol D in which 1% PVPP is added during leaf grinding.

Protocol H: Plant leaves are frozen in liquid nitrogen and homogenized in PBS containing 1 mM phenylmethylsulfonyl fluoride, 3 μg/ml pepstain, and 1 μg/ml leupeptin. After centrifugation at 20,000×g for 30 minutes at 4° C., the supernatants are used. Total protein concentration can be determined using standard procedures.

Once the protein extract is obtained, the sample is labeled with a suitable labeling agent, such as biotin, to produce a modified biological sample. The modified biological sample is contacted with target antigen-bound microparticles. The target antigen-bound microparticles are microparticles conjugated directly or indirectly (such as via an antibody) to the target antigen of interest. The target antigen bound-microparticles bind antigen-specific antibodies in the modified biological sample to form labeled microparticle complexes if the antigen-specific antibodies are present in the biological sample. The labeled microparticle complexes are detected according to known procedures, such as those described herein. An increase in detection of the labeled microparticle complexes relative to a reference level of microparticle complexes indicates the biological sample contains antigen-specific antibodies.

This disclosure provides a method of detecting antigen-specific antibodies in a serum sample. It will be apparent that the precise details of the methods described may be varied or modified without departing from the spirit of the described disclosure. We claim all such modifications and variations that fall within the scope and spirit of the claims below.

The invention claimed is:

1. A method for detecting antigen-specific antibodies in a biological sample, wherein the antigen-specific antibodies specifically bind to a target antigen, the method comprising:
   (i) providing a modified biological sample from an organism that is suspected of containing antibodies specific for the target antigen, wherein the biological sample from the organism has been modified by exposing it to a labeling agent that adds labels to antibodies that are present in the biological sample;
   (ii) contacting target antigen-bound microparticles with the modified biological sample, wherein the target antigen bound-microparticles bind antigen-specific labeled antibodies in the modified biological sample to form microparticle complexes if the antigen-specific antibodies are present in the biological sample; and
   (iii) detecting the microparticle complexes, wherein an increase in detection of the microparticle complexes with the antigen-specific labeled antibodies, relative to a reference level of microparticle complexes, indicates the biological sample contains antibodies specific for the target antigen.

2. The method of claim 1, wherein the labeling agent comprises a first specific binding partner, wherein the first specific binding partner is capable of binding to a second specific binding partner that carries a detectable label, and wherein detecting the microparticle complexes comprises exposing the microparticle complexes to the second specific binding partner that carries the detectable label and detecting a signal from the label if the antigen-specific antibodies are present in the biological sample.

3. The method of claim 2, wherein the first and second specific binding partners are selected from the group consisting of avidin and biotin.

4. The method of claim 3, wherein the first specific binding partner is biotin and the second specific binding partner is avidin.

5. The method of claim 4, wherein providing a modified biological sample comprises biotinylating the biological sample to add a biotin label to the antibodies that are present in the biological sample, and wherein the detectable label is bound to avidin, and the avidin binds to the biotin to add the detectable label to the antibodies that are present in the biological sample.

6. The method of claim 2, wherein the detectable label is a fluorophore.

7. The method of claim 6, wherein the first specific binding partner is biotin.

8. The method of claim 1, wherein the target antigen-bound microparticles comprise the target antigen bound to an antibody that binds the target antigen, and a microparticle coupled to the antibody.

9. The method of claim 1, wherein the target antigen-bound microparticles comprise a target antigen covalently bound to a microparticle.

10. The method of claim 1, wherein the biological sample is obtained from a mammalian species, a reptilian species, an avian species, a plant or an insect.

11. The method of claim 10, wherein the antigen-specific antibody is an engineered antibody.

12. The method of claim 1, wherein the target antigen is from a pathogen.

13. The method of claim 12, wherein the pathogen is a virus.

14. The method of claim 13, wherein the virus is a flavivirus.

15. The method of claim 14, wherein the target antigen is the flavivirus prM-E protein.

16. The method of claim 1, wherein the microparticles are polystyrene microspheres, carboxylated microspheres or magnetic beads.

17. The method of claim 1, wherein the microparticles are about 1 to about 100 microns in diameter.

18. The method of claim 1, wherein the microparticle complexes are detected using a flow instrument or a plate-based immunological assay.

19. The method of claim 1, wherein the reference level of microparticle complexes is determined using control antigen-bound microparticle complexes, wherein the reference level of microparticle complexes is determined by contacting target antigen-bound microparticles with a modified negative control biological sample.

20. The method of claim 1, wherein the biological sample is a bodily fluid sample.

21. The method of claim 1, wherein the organism is a human subject.

22. The method of claim 1, wherein the organism is a veterinary subject.

23. A method for detecting antigen-specific antibodies in a biological sample, wherein the antigen-specific antibodies specifically bind to a target antigen, the method comprising:
   (i) providing a biotinylated biological sample from an organism that is suspected of containing antibodies specific for the target antigen, wherein biotinylation labels antibodies that are present in the biological sample with biotin;
   (ii) contacting target antigen-bound microparticles with the biotinylated biological sample, wherein the target antigen bound-microparticles bind antigen-specific antibodies to form microparticle complexes if the antigen-specific antibodies are present in the biological sample;
   (iii) contacting the microparticle complexes with a biotin binding partner conjugated to a detectable label; and
   (iv) detecting the microparticle complexes, wherein detection of the microparticle complexes comprising detecting a signal from the detectable label if the antigen-specific antibodies are present in the biological sample, and wherein an increase in detection of the microparticle complexes relative to control microparticle complexes indicates the biological sample contains antigen-specific antibodies.

24. The method of claim 23, wherein the organism is a human subject.

25. The method of claim 23, wherein the organism is a veterinary subject.

* * * * *